(12) United States Patent
Gulevich et al.

(10) Patent No.: US 7,820,415 B2
(45) Date of Patent: Oct. 26, 2010

(54) METHOD FOR PRODUCING AN L-AMINO ACID USING A BACTERIUM OF THE ENTEROBACTERIACEAE FAMILY WITH ATTENUATED EXPRESSION OF THE YDIN GENE OR THE YDIB GENE OR COMBINATION THEREOF

(75) Inventors: Andrey Yurievich Gulevich, Moscow (RU); Tatyana Aleksandrovna Gaydenko, Moscow (RU); Vladimir Yurievich Ermishev, Moscow (RU); Aleksandra Yurievna Skorokhodova, Moscow (RU); Irina Vladimirovna Biryukova, Moscow (RU); Sergei Vladimirovich Mashko, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/372,060

(22) Filed: Feb. 17, 2009

(65) Prior Publication Data
US 2009/0191601 A1 Jul. 30, 2009

Related U.S. Application Data

(63) Continuation of application No. PCT/JP2007/066322, filed on Aug. 16, 2007.

(30) Foreign Application Priority Data
Aug. 16, 2006 (RU) ............................... 2006129690

(51) Int. Cl.
*C12N 1/21* (2006.01)
*C12P 13/04* (2006.01)
*C12P 13/22* (2006.01)

(52) U.S. Cl. .................... 435/108; 435/106; 435/252.3; 435/252.33

(58) Field of Classification Search ................. 435/108, 435/106, 252.3, 252.33
See application file for complete search history.

(56) References Cited

U.S. PATENT DOCUMENTS

| | | | |
|---|---|---|---|
| 4,681,852 A | 7/1987 | Tribe |
| 5,168,056 A | 12/1992 | Frost |
| 5,618,716 A | 4/1997 | Burlingame |
| 5,776,736 A | 7/1998 | Frost et al. |
| 5,856,148 A | 1/1999 | Burlingame |
| 5,906,925 A | 5/1999 | Liao |
| 5,985,617 A | 11/1999 | Liao |
| 6,180,373 B1 | 1/2001 | Wich et al. |
| 6,319,696 B1 | 11/2001 | Kishino et al. |
| 6,436,664 B1 | 8/2002 | Iomantas et al. |
| 6,489,100 B1 | 12/2002 | Liao |
| 6,960,455 B2 | 11/2005 | Livshits et al. |
| 7,045,320 B2 | 5/2006 | Iwatani et al. |
| 7,179,623 B2 | 2/2007 | Livshits et al. |
| 7,259,003 B2 | 8/2007 | Livshits et al. |
| 7,300,776 B2 | 11/2007 | Ito et al. |
| 2002/0155521 A1 | 10/2002 | Valle et al. |
| 2003/0157667 A1 | 8/2003 | Vitushkina et al. |
| 2005/0181488 A1 | 8/2005 | Akhverdian et al. |
| 2005/0191684 A1 | 9/2005 | Zimenkov et al. |
| 2006/0014257 A1 | 1/2006 | Katashkina et al. |
| 2006/0035348 A1 | 2/2006 | Gulevich et al. |
| 2006/0063240 A1 | 3/2006 | Katashkina et al. |
| 2006/0088919 A1 | 4/2006 | Rybak et al. |
| 2006/0234358 A1 | 10/2006 | Anderlei et al. |
| 2008/0113416 A1 | 5/2008 | Filippov et al. |
| 2008/0153138 A1 | 6/2008 | Livshits et al. |

FOREIGN PATENT DOCUMENTS

| | | |
|---|---|---|
| EP | 0763127 | 3/1997 |
| EP | 1 038 968 | 9/2000 |
| EP | 1270721 | 1/2003 |
| WO | WO00/73484 | 12/2000 |
| WO | WO03/093490 | 11/2003 |
| WO | WO2005/103275 | 3/2005 |
| WO | WO96/34961 | 11/2006 |
| WO | WO2008/020650 | 2/2008 |

OTHER PUBLICATIONS

Benach, J., et al., "The 2.3-Å Crystal Structure of the Shikimate 5-Dehydrogenase Orthologue YdiB from *Escherichia coli* Suggests a Novel Catalytic Environment for an NAD-dependent Dehydrogenase," J. Biol. Chem 2003;278(21):19176-19182.
Ikeda, M., Advances in Biochemical Engineering/Biotechnology, Springer, Berlin, DE, vol. 79, 2003, pp. 1-35.
Johansson, L., et al., "Transcriptome analysis of a shikimic acid producing strain of *Escherichia coli* W3110 grown under carbon- and phosphate-limited conditions," J. Biotechnol. 2006;126:528-545.
Johansson, L., et al., "Shikimic Acid Production by a Modified Strain of *E. coli* (W3110.shik1) Under Phosphate-Limited and Carbon-Limited Conditions," Biotechnol. And Bioeng. 2005;92(5):541-552.
Lequeux, G., et al., "MFA for Overdetermined Systems Reviewed and Compared with RNA Expression Data to Elucidate the Difference in Shikimate Yield between Carbon- and Phosphate-Limited Continuous Cultures of *E. coli* W3110.shik1," Biotechnol. Prog. 2006;22:1056-1070.
Lindner, H. A., et al., "Site-directed Mutagenesis of the Active Site Region in the Quinate/Shikimate 5-Dehydrogenase YdiB of *Escherichia coli*," J. Biol. Chem. 2005;280(8):7162-7169.
Michel, G., et al., "Structures of Shikimate Dehydrogenase AroE and Its Paralog YdiB," J. Biol. Chem. 2003;278(21):19463-19472.
International Search Report for PCT Patent App. No. PCT/JP2007/066322 (Dec. 5, 2007).
International Preliminary Report on Patentability for PCT Patent App. No. PCT/JP2007/066322 (Feb. 26, 2009).

(Continued)

*Primary Examiner*—Tekchand Saidha
(74) *Attorney, Agent, or Firm*—Shelly Guest Cermak; Cermak Nakajima LLP

(57) ABSTRACT

The present invention provides a method for producing an aromatic L-amino acid using a bacterium of the Enterobacteriaceae family, particularly a bacterium belonging to genus *Escherichia* or *Pantoea*, which has been modified to attenuate expression of the ydiN gene, the ydiB gene, or both.

11 Claims, 2 Drawing Sheets

OTHER PUBLICATIONS

U.S. Appl. No. 09/979,864, Romeo et al., Filed Feb. 26, 2002.
U.S. Appl. No. 11/830,969, Gulevich et al., Filed Jul. 31, 2007.
U.S. Appl. No. 11/952,297, Rybak et al., Filed Dec. 7, 2007.
U.S. Appl. No. 12/017,379, Rybak et al., Filed Jan. 22, 2008.
U.S. Appl. No. 12/022,299, Rybak et al., Filed Jan. 30, 2008.
U.S. Appl. No. 61/046,081, Gulevich et al., Filed Apr. 18, 2008.
U.S. Appl. No. 61/058,313, Ermishev et al., Filed Jun. 3, 2008.
U.S. Appl. No. 12/212,743, Rybak et al., Filed Sep. 18, 2008.
U.S. Appl. No. 12/253,415, Filippov et al., Filed Oct. 17, 2008.
U.S. Appl. No. 12/372,060, Gulevich et al., Filed Feb. 17, 2009.
U.S. Appl. No. 12/388,568, Gulevich et al., Filed Feb. 19, 2009.

SEQUENCE LISTING

<160> NUMBER OF SEQ ID NOS: 21

<210> SEQ ID NO 1
<211> LENGTH: 1266
<212> TYPE: DNA
<213> ORGANISM: Escherichia coli
<220> FEATURE:
<221> NAME/KEY: CDS
<222> LOCATION: (1)..(1266)

<400> SEQUENCE: 1

```
atg tct caa aat aag gct ttc agc acg cca ttt atc ctg gct gtt ctt        48
Met Ser Gln Asn Lys Ala Phe Ser Thr Pro Phe Ile Leu Ala Val Leu
1               5                   10                  15 tgt att tac ttc agc tac ttc ctg cac ggc att agt gtt att acg ctt        96
Cys Ile Tyr Phe Ser Tyr Phe Leu His Gly Ile Ser Val Ile Thr Leu
```

-continued

```
                  20                  25                  30
gcc caa aat atg tca tct ctg gcg gaa aag ttt tcc act gac aac gcg    144
Ala Gln Asn Met Ser Ser Leu Ala Glu Lys Phe Ser Thr Asp Asn Ala
             35                  40                  45 ggc att gcc tac tta att tcc ggt atc ggt ttg ggg cga ttg atc agt    192
Gly Ile Ala Tyr Leu Ile Ser Gly Ile Gly Leu Gly Arg Leu Ile Ser
 50                  55                  60 att tta ttc ttc ggt gtg atc tcc gat aag ttt ggt cgt cgg gcg gtg    240
Ile Leu Phe Phe Gly Val Ile Ser Asp Lys Phe Gly Arg Arg Ala Val
 65                  70                  75                  80 ata tta atg gca gta ata atg tat ctg cta ttc ttc ttt ggt att ccc    288
Ile Leu Met Ala Val Ile Met Tyr Leu Leu Phe Phe Phe Gly Ile Pro
                 85                  90                  95 gct tgc ccg aat tta act ctc gcc tac ggt ctg gca gtg tgc gta ggt    336
Ala Cys Pro Asn Leu Thr Leu Ala Tyr Gly Leu Ala Val Cys Val Gly
                100                 105                 110 atc gct aac tca gcg ctg gat acg ggt ggc tac ccc gcg ctc atg gaa    384
Ile Ala Asn Ser Ala Leu Asp Thr Gly Gly Tyr Pro Ala Leu Met Glu
                115                 120                 125 tgc ttt ccg aaa gcc tct ggt tcg gcg gtc ata ctg gtt aaa gcg atg    432
Cys Phe Pro Lys Ala Ser Gly Ser Ala Val Ile Leu Val Lys Ala Met
130                 135                 140 gtg tca ttt ggg caa atg ttc tac cca atg ctg gtg agc tat atg ttg    480
Val Ser Phe Gly Gln Met Phe Tyr Pro Met Leu Val Ser Tyr Met Leu
145                 150                 155                 160 ctc aat aat atc tgg tac ggc tat ggg ctg att att ccg ggt att cta    528
Leu Asn Asn Ile Trp Tyr Gly Tyr Gly Leu Ile Ile Pro Gly Ile Leu
                165                 170                 175 ttt gta ctg atc acg ctg atg ctg ttg aaa agc aaa ttc ccc agc cag    576
Phe Val Leu Ile Thr Leu Met Leu Leu Lys Ser Lys Phe Pro Ser Gln
                180                 185                 190 ttg gtg gac gcc agc gta act aat gaa tta ccg caa atg aac agc aaa    624
Leu Val Asp Ala Ser Val Thr Asn Glu Leu Pro Gln Met Asn Ser Lys
                195                 200                 205 ccg tta gtc tgg ctg gaa ggt gtt tca tcg gta ctg ttc ggt gta gcc    672
Pro Leu Val Trp Leu Glu Gly Val Ser Ser Val Leu Phe Gly Val Ala
210                 215                 220 gca ttc tcg acc ttt tat gtg att gtg gtg tgg atg ccc aaa tat gcg    720
Ala Phe Ser Thr Phe Tyr Val Ile Val Val Trp Met Pro Lys Tyr Ala
225                 230                 235                 240 atg gct ttt gct ggt atg tca gaa gct gag gca tta aaa acc atc tct    768
Met Ala Phe Ala Gly Met Ser Glu Ala Glu Ala Leu Lys Thr Ile Ser
                245                 250                 255 tat tac agt atg ggc tcg ttg gtc tgt gtc ttt att ttt gcc gca cta    816
Tyr Tyr Ser Met Gly Ser Leu Val Cys Val Phe Ile Phe Ala Ala Leu
                260                 265                 270 ctg aaa aaa atg gtc cgg ccc atc tgg gct aat gta ttt aac tct gca    864
Leu Lys Lys Met Val Arg Pro Ile Trp Ala Asn Val Phe Asn Ser Ala
                275                 280                 285 ctg gca aca ata aca gca gcc att atc tac ctg tac cct tct cca ctg    912
Leu Ala Thr Ile Thr Ala Ala Ile Ile Tyr Leu Tyr Pro Ser Pro Leu
                290                 295                 300 gtg tgc aat gcc gga gcc ttt gtt atc ggt ttc tca gca gct ggc ggc    960
Val Cys Asn Ala Gly Ala Phe Val Ile Gly Phe Ser Ala Ala Gly Gly
305                 310                 315                 320 att tta cag ctc ggc gtt tcg gtc atg tca gag ttt ttt ccc aaa agc    1008
Ile Leu Gln Leu Gly Val Ser Val Met Ser Glu Phe Phe Pro Lys Ser
                325                 330                 335 aaa gcc aaa gtc acc agt att tat atg atg atg ggt gga ctg gct aac    1056
Lys Ala Lys Val Thr Ser Ile Tyr Met Met Met Gly Gly Leu Ala Asn
```

```
Lys Ala Lys Val Thr Ser Ile Tyr Met Met Met Gly Gly Leu Ala Asn
            340                 345                 350 ttt gtt att cca ctg att acc ggt tat ctg tcg aac atc ggc ctg caa    1104
Phe Val Ile Pro Leu Ile Thr Gly Tyr Leu Ser Asn Ile Gly Leu Gln
            355                 360                 365 tat atc att gtt ctc gat ttt act ttc gcg ctg ctg gcc ctg att acc    1152
Tyr Ile Ile Val Leu Asp Phe Thr Phe Ala Leu Leu Ala Leu Ile Thr
            370                 375                 380 gca att att gtt ttt atc cgc tat tac cgc gtt ttc att att cct gaa    1200
Ala Ile Ile Val Phe Ile Arg Tyr Tyr Arg Val Phe Ile Ile Pro Glu
385                 390                 395                 400 aat gat gtg cgg ttt ggc gag cgt aaa ttt tgc acc cgg tta aac aca    1248
Asn Asp Val Arg Phe Gly Glu Arg Lys Phe Cys Thr Arg Leu Asn Thr
                    405                 410                 415 att aag cat aga ggt taa                                            1266
Ile Lys His Arg Gly
            420

<210> SEQ ID NO 2
<211> LENGTH: 421
<212> TYPE: PRT
<213> ORGANISM: Escherichia coli

<400> SEQUENCE: 2

Met Ser Gln Asn Lys Ala Phe Ser Thr Pro Phe Ile Leu Ala Val Leu
1               5                   10                  15

Cys Ile Tyr Phe Ser Tyr Phe Leu His Gly Ile Ser Val Ile Thr Leu
            20                  25                  30

Ala Gln Asn Met Ser Ser Leu Ala Glu Lys Phe Ser Thr Asp Asn Ala
        35                  40                  45

Gly Ile Ala Tyr Leu Ile Ser Gly Ile Gly Leu Gly Arg Leu Ile Ser
    50                  55                  60

Ile Leu Phe Phe Gly Val Ile Ser Asp Lys Phe Gly Arg Arg Ala Val
65                  70                  75                  80

Ile Leu Met Ala Val Ile Met Tyr Leu Leu Phe Phe Phe Gly Ile Pro
                85                  90                  95

Ala Cys Pro Asn Leu Thr Leu Ala Tyr Gly Leu Ala Val Cys Val Gly
            100                 105                 110

Ile Ala Asn Ser Ala Leu Asp Thr Gly Gly Tyr Pro Ala Leu Met Glu
        115                 120                 125

Cys Phe Pro Lys Ala Ser Gly Ser Ala Val Ile Leu Val Lys Ala Met
    130                 135                 140

Val Ser Phe Gly Gln Met Phe Tyr Pro Met Leu Val Ser Tyr Met Leu
145                 150                 155                 160

Leu Asn Asn Ile Trp Tyr Gly Tyr Gly Leu Ile Ile Pro Gly Ile Leu
                165                 170                 175

Phe Val Leu Ile Thr Leu Met Leu Leu Lys Ser Lys Phe Pro Ser Gln
            180                 185                 190

Leu Val Asp Ala Ser Val Thr Asn Glu Leu Pro Gln Met Asn Ser Lys
        195                 200                 205

Pro Leu Val Trp Leu Glu Gly Val Ser Ser Val Leu Phe Gly Val Ala
    210                 215                 220

Ala Phe Ser Thr Phe Tyr Val Ile Val Val Trp Met Pro Lys Tyr Ala
225                 230                 235                 240

Met Ala Phe Ala Gly Met Ser Glu Ala Glu Ala Leu Lys Thr Ile Ser
                245                 250                 255
```

```
Tyr Tyr Ser Met Gly Ser Leu Val Cys Val Phe Ile Phe Ala Ala Leu
            260                 265                 270

Leu Lys Lys Met Val Arg Pro Ile Trp Ala Asn Val Phe Asn Ser Ala
        275                 280                 285

Leu Ala Thr Ile Thr Ala Ala Ile Ile Tyr Leu Tyr Pro Ser Pro Leu
    290                 295                 300

Val Cys Asn Ala Gly Ala Phe Val Ile Gly Phe Ser Ala Ala Gly Gly
305                 310                 315                 320

Ile Leu Gln Leu Gly Val Ser Val Met Ser Glu Phe Phe Pro Lys Ser
                325                 330                 335

Lys Ala Lys Val Thr Ser Ile Tyr Met Met Met Gly Gly Leu Ala Asn
            340                 345                 350

Phe Val Ile Pro Leu Ile Thr Gly Tyr Leu Ser Asn Ile Gly Leu Gln
        355                 360                 365

Tyr Ile Ile Val Leu Asp Phe Thr Phe Ala Leu Leu Ala Leu Ile Thr
    370                 375                 380

Ala Ile Ile Val Phe Ile Arg Tyr Tyr Arg Val Phe Ile Ile Pro Glu
385                 390                 395                 400

Asn Asp Val Arg Phe Gly Glu Arg Lys Phe Cys Thr Arg Leu Asn Thr
                405                 410                 415

Ile Lys His Arg Gly
            420

<210> SEQ ID NO 3
<211> LENGTH: 867
<212> TYPE: DNA
<213> ORGANISM: Escherichia coli
<220> FEATURE:
<221> NAME/KEY: CDS
<222> LOCATION: (1)..(867)

<400> SEQUENCE: 3 atg gat gtt acc gca aaa tac gaa ttg att ggg ttg atg gcc tat cct      48
Met Asp Val Thr Ala Lys Tyr Glu Leu Ile Gly Leu Met Ala Tyr Pro
1               5                   10                  15 atc cgc cac agt tta tcg ccc gaa atg cag aat aaa gcc tta gaa aaa      96
Ile Arg His Ser Leu Ser Pro Glu Met Gln Asn Lys Ala Leu Glu Lys
                20                  25                  30 gcg gga ttg cca ttt acc tat atg gcc ttc gaa gtg gat aac gat agc     144
Ala Gly Leu Pro Phe Thr Tyr Met Ala Phe Glu Val Asp Asn Asp Ser
            35                  40                  45 ttt cct gga gca att gaa gga tta aaa gcc ctc aaa atg cgc gga act     192
Phe Pro Gly Ala Ile Glu Gly Leu Lys Ala Leu Lys Met Arg Gly Thr
        50                  55                  60 ggt gta tcg atg ccg aac aaa caa ctg gcg tgt gaa tat gtt gat gaa     240
Gly Val Ser Met Pro Asn Lys Gln Leu Ala Cys Glu Tyr Val Asp Glu
65                  70                  75                  80 tta aca cca gct gcc aaa ctg gtg ggg gcc atc aac acc atc gtt aat     288
Leu Thr Pro Ala Ala Lys Leu Val Gly Ala Ile Asn Thr Ile Val Asn
                85                  90                  95 gat gat ggc tat ctg cgt ggc tat aac acc gac ggc acg ggc cat att     336
Asp Asp Gly Tyr Leu Arg Gly Tyr Asn Thr Asp Gly Thr Gly His Ile
                100                 105                 110 cgc gcc att aaa gag agc ggt ttt gat atc aaa ggc aaa acg atg gtg     384
Arg Ala Ile Lys Glu Ser Gly Phe Asp Ile Lys Gly Lys Thr Met Val
            115                 120                 125 ctg tta ggg gcc ggt ggt gcc tca acg gca att ggc gcg cag ggg gca     432
Leu Leu Gly Ala Gly Gly Ala Ser Thr Ala Ile Gly Ala Gln Gly Ala
        130                 135                 140
```

```
att gaa ggt tta aaa gaa att aaa ctc ttt aac cgt cgg gat gag ttc      480
Ile Glu Gly Leu Lys Glu Ile Lys Leu Phe Asn Arg Arg Asp Glu Phe
145                 150                 155                 160 ttc gat aaa gcc ctc gcc ttc gcg cag cgg gtt aat gaa aac acc gat      528
Phe Asp Lys Ala Leu Ala Phe Ala Gln Arg Val Asn Glu Asn Thr Asp
                165                 170                 175 tgt gtc gtc acg gtc acc gat ctc gcc gat cag caa gcc ttt gct gaa      576
Cys Val Val Thr Val Thr Asp Leu Ala Asp Gln Gln Ala Phe Ala Glu
            180                 185                 190 gcc ctg gct tcc gcc gac att tta acc aat ggc aca aaa gtg ggt atg      624
Ala Leu Ala Ser Ala Asp Ile Leu Thr Asn Gly Thr Lys Val Gly Met
        195                 200                 205 aaa ccc ctt gag aat gaa tca ttg gtt aat gat atc agt ctg tta cat      672
Lys Pro Leu Glu Asn Glu Ser Leu Val Asn Asp Ile Ser Leu Leu His
    210                 215                 220 ccg gga ctt ctg gtc act gaa tgc gtg tat aac ccg cat atg acg aag      720
Pro Gly Leu Leu Val Thr Glu Cys Val Tyr Asn Pro His Met Thr Lys
225                 230                 235                 240 tta ttg cag cag gcg caa caa gct ggt tgc aaa acg att gat gga tac      768
Leu Leu Gln Gln Ala Gln Gln Ala Gly Cys Lys Thr Ile Asp Gly Tyr
                245                 250                 255 ggc atg ttg ttg tgg caa ggg gct gaa cag ttc aca tta tgg act ggc      816
Gly Met Leu Leu Trp Gln Gly Ala Glu Gln Phe Thr Leu Trp Thr Gly
            260                 265                 270 aaa gat ttc cct ctg gaa tat gtt aaa cag gtc atg ggg ttc ggt gcc      864
Lys Asp Phe Pro Leu Glu Tyr Val Lys Gln Val Met Gly Phe Gly Ala
        275                 280                 285 tga                                                                   867
```

<210> SEQ ID NO 4
<211> LENGTH: 288
<212> TYPE: PRT
<213> ORGANISM: Escherichia coli

<400> SEQUENCE: 4

```
Met Asp Val Thr Ala Lys Tyr Glu Leu Ile Gly Leu Met Ala Tyr Pro
1               5                   10                  15

Ile Arg His Ser Leu Ser Pro Glu Met Gln Asn Lys Ala Leu Glu Lys
            20                  25                  30

Ala Gly Leu Pro Phe Thr Tyr Met Ala Phe Glu Val Asp Asn Asp Ser
        35                  40                  45

Phe Pro Gly Ala Ile Glu Gly Leu Lys Ala Leu Lys Met Arg Gly Thr
    50                  55                  60

Gly Val Ser Met Pro Asn Lys Gln Leu Ala Cys Glu Tyr Val Asp Glu
65                  70                  75                  80

Leu Thr Pro Ala Ala Lys Leu Val Gly Ala Ile Asn Thr Ile Val Asn
                85                  90                  95

Asp Asp Gly Tyr Leu Arg Gly Tyr Asn Thr Asp Gly Thr Gly His Ile
            100                 105                 110

Arg Ala Ile Lys Glu Ser Gly Phe Asp Ile Lys Gly Lys Thr Met Val
        115                 120                 125

Leu Leu Gly Ala Gly Gly Ala Ser Thr Ala Ile Gly Ala Gln Gly Ala
    130                 135                 140

Ile Glu Gly Leu Lys Glu Ile Lys Leu Phe Asn Arg Arg Asp Glu Phe
145                 150                 155                 160

Phe Asp Lys Ala Leu Ala Phe Ala Gln Arg Val Asn Glu Asn Thr Asp
                165                 170                 175
```

Cys Val Val Thr Val Thr Asp Leu Ala Asp Gln Gln Ala Phe Ala Glu
            180                 185                 190

Ala Leu Ala Ser Ala Asp Ile Leu Thr Asn Gly Thr Lys Val Gly Met
        195                 200                 205

Lys Pro Leu Glu Asn Glu Ser Leu Val Asn Asp Ile Ser Leu Leu His
    210                 215                 220

Pro Gly Leu Leu Val Thr Glu Cys Val Tyr Asn Pro His Met Thr Lys
225                 230                 235                 240

Leu Leu Gln Gln Ala Gln Gln Ala Gly Cys Lys Thr Ile Asp Gly Tyr
                245                 250                 255

Gly Met Leu Leu Trp Gln Gly Ala Glu Gln Phe Thr Leu Trp Thr Gly
            260                 265                 270

Lys Asp Phe Pro Leu Glu Tyr Val Lys Gln Val Met Gly Phe Gly Ala
        275                 280                 285

<210> SEQ ID NO 5
<211> LENGTH: 41
<212> TYPE: DNA
<213> ORGANISM: Artificial
<220> FEATURE:
<223> OTHER INFORMATION: primer P1

<400> SEQUENCE: 5
gtatggtcta aaggagcag acatgaatta tcagaacgac g           41

<210> SEQ ID NO 6
<211> LENGTH: 36
<212> TYPE: DNA
<213> ORGANISM: Artificial
<220> FEATURE:
<223> OTHER INFORMATION: primer P2

<400> SEQUENCE: 6
gacaatcccg ggttacccgc gacgcgcttt tactgc              36

<210> SEQ ID NO 7
<211> LENGTH: 39
<212> TYPE: DNA
<213> ORGANISM: Artificial
<220> FEATURE:
<223> OTHER INFORMATION: primer P3

<400> SEQUENCE: 7
caacatcccg ggaagacagg attgggtaaa tggcaaagg            39

<210> SEQ ID NO 8
<211> LENGTH: 47
<212> TYPE: DNA
<213> ORGANISM: Artificial
<220> FEATURE:
<223> OTHER INFORMATION: primer P4

<400> SEQUENCE: 8
ccgttggagc tcgcatgcgt cgacttacag cagacgggcg cgaatgg      47

<210> SEQ ID NO 9
<211> LENGTH: 66
<212> TYPE: DNA
<213> ORGANISM: Artificial
<220> FEATURE:
<223> OTHER INFORMATION: primer P5

<400> SEQUENCE: 9

```
gtgaaaatgt ctcaaaataa ggctttcagc acgccattcg ctcaagttag tataaaaaag    60
ctgaac                                                                66

<210> SEQ ID NO 10
<211> LENGTH: 64
<212> TYPE: DNA
<213> ORGANISM: Artificial
<220> FEATURE:
<223> OTHER INFORMATION: primer P6

<400> SEQUENCE: 10
ttaacctcta tgcttaattg tgtttaaccg ggtgcatgaa gcctgctttt ttatactaag    60
ttgg                                                                  64

<210> SEQ ID NO 11
<211> LENGTH: 23
<212> TYPE: DNA
<213> ORGANISM: Artificial
<220> FEATURE:
<223> OTHER INFORMATION: primer P7

<400> SEQUENCE: 11
gtaaaccgtc ggagaacaat acg                                             23

<210> SEQ ID NO 12
<211> LENGTH: 23
<212> TYPE: DNA
<213> ORGANISM: Artificial
<220> FEATURE:
<223> OTHER INFORMATION: primer P8

<400> SEQUENCE: 12
gccatatagg taaatggcaa tcc                                             23

<210> SEQ ID NO 13
<211> LENGTH: 66
<212> TYPE: DNA
<213> ORGANISM: Artificial
<220> FEATURE:
<223> OTHER INFORMATION: primer P9

<400> SEQUENCE: 13
atggatgtta ccgcaaaata cgaattgatt gggttgttcg ctcaagttag tataaaaaag    60
ctgaac                                                                66

<210> SEQ ID NO 14
<211> LENGTH: 64
<212> TYPE: DNA
<213> ORGANISM: Artificial
<220> FEATURE:
<223> OTHER INFORMATION: primer P10

<400> SEQUENCE: 14
tcaggcaccg aacccatga cctgtttaac atattctgaa gcctgctttt ttatactaag    60
ttgg                                                                  64

<210> SEQ ID NO 15
<211> LENGTH: 23
<212> TYPE: DNA
<213> ORGANISM: Artificial
<220> FEATURE:
<223> OTHER INFORMATION: primer P11
```

<400> SEQUENCE: 15
cctgaaaatg atgtgcggtt tgg                                             23

<210> SEQ ID NO 16
<211> LENGTH: 20
<212> TYPE: DNA
<213> ORGANISM: Artificial
<220> FEATURE:
<223> OTHER INFORMATION: primer P12

<400> SEQUENCE: 16
gagcttcgga tttcacgctg                                                 20

<210> SEQ ID NO 17
<211> LENGTH: 1233
<212> TYPE: DNA
<213> ORGANISM: Escherichia coli
<220> FEATURE:
<221> NAME/KEY: CDS
<222> LOCATION: (1)..(1233)

<400> SEQUENCE: 17

```
atg gca aag gta tcg ctg gag aaa gac aag att aag ttt ctg ctg gta        48
Met Ala Lys Val Ser Leu Glu Lys Asp Lys Ile Lys Phe Leu Leu Val
 1               5                  10                  15 gaa ggc gtg cac caa aag gcg ctg gaa agc ctt cgt gca gct ggt tac        96
Glu Gly Val His Gln Lys Ala Leu Glu Ser Leu Arg Ala Ala Gly Tyr
             20                  25                  30 acc aac atc gaa ttt cac aaa ggc gcg ctg gat gat gaa caa tta aaa       144
Thr Asn Ile Glu Phe His Lys Gly Ala Leu Asp Asp Glu Gln Leu Lys
         35                  40                  45 gaa tcc atc cgc gat gcc cac ttc atc ggc ctg cga tcc cgt acc cat       192
Glu Ser Ile Arg Asp Ala His Phe Ile Gly Leu Arg Ser Arg Thr His
     50                  55                  60 ctg act gaa gac gtg atc aac gcc gca gaa aaa ctg gtc gct att ggc       240
Leu Thr Glu Asp Val Ile Asn Ala Ala Glu Lys Leu Val Ala Ile Gly
 65                  70                  75                  80 tgt ttc tgt atc gga aca aac cag gtt gat ctg gat gcg gcg gca aag       288
Cys Phe Cys Ile Gly Thr Asn Gln Val Asp Leu Asp Ala Ala Ala Lys
                 85                  90                  95 cgc ggg atc ccg gta ttt aac gca ccg ttc tca aat acg cgc tct gtt       336
Arg Gly Ile Pro Val Phe Asn Ala Pro Phe Ser Asn Thr Arg Ser Val
            100                 105                 110 gcg gag ctg gtg att ggc gaa ctg ctg ctg cta ttg cgc ggc gtg ccg       384
Ala Glu Leu Val Ile Gly Glu Leu Leu Leu Leu Arg Gly Val Pro
        115                 120                 125 gaa gcc aat gct aaa gcg cac cgt ggc gtg tgg aac aaa ctg gcg gcg       432
Glu Ala Asn Ala Lys Ala His Arg Gly Val Trp Asn Lys Leu Ala Ala
    130                 135                 140 ggt tct ttt gaa gcg cgc ggc aaa aag ctg ggt atc atc ggc tac ggt       480
Gly Ser Phe Glu Ala Arg Gly Lys Lys Leu Gly Ile Ile Gly Tyr Gly
145                 150                 155                 160 cat att ggt acg caa ttg ggc att ctg gct gaa tcg ctg gga atg tat       528
His Ile Gly Thr Gln Leu Gly Ile Leu Ala Glu Ser Leu Gly Met Tyr
                165                 170                 175 gtt tac ttt tat gat att gaa aat aaa ctg ccg ctg ggc aac gcc act       576
Val Tyr Phe Tyr Asp Ile Glu Asn Lys Leu Pro Leu Gly Asn Ala Thr
            180                 185                 190 cag gta cag cat ctt tct gac ctg ctg aat atg agc gat gtg gtg agt       624
Gln Val Gln His Leu Ser Asp Leu Leu Asn Met Ser Asp Val Val Ser
        195                 200                 205
```

```
ctg cat gta cca gag aat ccg tcc acc aaa aat atg atg ggc gcg aaa      672
Leu His Val Pro Glu Asn Pro Ser Thr Lys Asn Met Met Gly Ala Lys
    210                 215                 220 gaa att tca cta atg aag ccc ggc tcg ctg ctg att aat gct tcg cgc      720
Glu Ile Ser Leu Met Lys Pro Gly Ser Leu Leu Ile Asn Ala Ser Arg
225                 230                 235                 240 ggt act gtg gtg gat att ccg gcg ctg tgt gat gcg ctg gcg agc aaa      768
Gly Thr Val Val Asp Ile Pro Ala Leu Cys Asp Ala Leu Ala Ser Lys
                245                 250                 255 cat ctg gcg ggg gcg gca atc gac gta ttc ccg acg gaa ccg gcg acc      816
His Leu Ala Gly Ala Ala Ile Asp Val Phe Pro Thr Glu Pro Ala Thr
            260                 265                 270 aat agc gat cca ttt acc tct ccg ctg tgt gaa ttc gac aac gtc ctt      864
Asn Ser Asp Pro Phe Thr Ser Pro Leu Cys Glu Phe Asp Asn Val Leu
        275                 280                 285 ctg acg cca cac att ggc ggt tcg act cag gaa gcg cag gag aat atc      912
Leu Thr Pro His Ile Gly Gly Ser Thr Gln Glu Ala Gln Glu Asn Ile
    290                 295                 300 ggc ctg gaa gtt gcg ggt aaa ttg atc aag tat tct gac aat ggc tca      960
Gly Leu Glu Val Ala Gly Lys Leu Ile Lys Tyr Ser Asp Asn Gly Ser
305                 310                 315                 320 acg ctc tct gcg gtg aac ttc ccg gaa gtc tcg ctg cca ctg cac ggt     1008
Thr Leu Ser Ala Val Asn Phe Pro Glu Val Ser Leu Pro Leu His Gly
                325                 330                 335 ggg cgt cgt ctg atg cac atc cac gaa aac cgt ccg ggc gtg cta act     1056
Gly Arg Arg Leu Met His Ile His Glu Asn Arg Pro Gly Val Leu Thr
            340                 345                 350 gcg ctg aac aaa atc ttc gcc gag cag ggc gtc aac atc gcc gcg caa     1104
Ala Leu Asn Lys Ile Phe Ala Glu Gln Gly Val Asn Ile Ala Ala Gln
        355                 360                 365 tat ctg caa act tcc gcc cag atg ggt tat gtg gtt att gat att gaa     1152
Tyr Leu Gln Thr Ser Ala Gln Met Gly Tyr Val Val Ile Asp Ile Glu
    370                 375                 380 gcc gac gaa gac gtt gcc gaa aaa gcg ctg cag gca atg aaa gct att     1200
Ala Asp Glu Asp Val Ala Glu Lys Ala Leu Gln Ala Met Lys Ala Ile
385                 390                 395                 400 ccg ggt acc att cgc gcc cgt ctg ctg tac taa                         1233
Pro Gly Thr Ile Arg Ala Arg Leu Leu Tyr
                405                 410

<210> SEQ ID NO 18
<211> LENGTH: 410
<212> TYPE: PRT
<213> ORGANISM: Escherichia coli

<400> SEQUENCE: 18

Met Ala Lys Val Ser Leu Glu Lys Asp Lys Ile Lys Phe Leu Leu Val
1               5                   10                  15

Glu Gly Val His Gln Lys Ala Leu Glu Ser Leu Arg Ala Ala Gly Tyr
            20                  25                  30

Thr Asn Ile Glu Phe His Lys Gly Ala Leu Asp Asp Glu Gln Leu Lys
        35                  40                  45

Glu Ser Ile Arg Asp Ala His Phe Ile Gly Leu Arg Ser Arg Thr His
    50                  55                  60

Leu Thr Glu Asp Val Ile Asn Ala Ala Glu Lys Leu Val Ala Ile Gly
65                  70                  75                  80

Cys Phe Cys Ile Gly Thr Asn Gln Val Asp Leu Asp Ala Ala Ala Lys
                85                  90                  95

Arg Gly Ile Pro Val Phe Asn Ala Pro Phe Ser Asn Thr Arg Ser Val
```

```
                100                 105                 110
Ala Glu Leu Val Ile Gly Glu Leu Leu Leu Leu Arg Gly Val Pro
            115                 120                 125
Glu Ala Asn Ala Lys Ala His Arg Gly Val Trp Asn Lys Leu Ala Ala
        130                 135                 140
Gly Ser Phe Glu Ala Arg Gly Lys Lys Leu Gly Ile Ile Gly Tyr Gly
145                 150                 155                 160
His Ile Gly Thr Gln Leu Gly Ile Leu Ala Glu Ser Leu Gly Met Tyr
                165                 170                 175
Val Tyr Phe Tyr Asp Ile Glu Asn Lys Leu Pro Leu Gly Asn Ala Thr
            180                 185                 190
Gln Val Gln His Leu Ser Asp Leu Leu Asn Met Ser Asp Val Val Ser
        195                 200                 205
Leu His Val Pro Glu Asn Pro Ser Thr Lys Asn Met Met Gly Ala Lys
210                 215                 220
Glu Ile Ser Leu Met Lys Pro Gly Ser Leu Leu Ile Asn Ala Ser Arg
225                 230                 235                 240
Gly Thr Val Val Asp Ile Pro Ala Leu Cys Asp Ala Leu Ala Ser Lys
                245                 250                 255
His Leu Ala Gly Ala Ala Ile Asp Val Phe Pro Thr Glu Pro Ala Thr
            260                 265                 270
Asn Ser Asp Pro Phe Thr Ser Pro Leu Cys Glu Phe Asp Asn Val Leu
        275                 280                 285
Leu Thr Pro His Ile Gly Gly Ser Thr Gln Glu Ala Gln Glu Asn Ile
    290                 295                 300
Gly Leu Glu Val Ala Gly Lys Leu Ile Lys Tyr Ser Asp Asn Gly Ser
305                 310                 315                 320
Thr Leu Ser Ala Val Asn Phe Pro Glu Val Ser Leu Pro Leu His Gly
                325                 330                 335
Gly Arg Arg Leu Met His Ile His Glu Asn Arg Pro Gly Val Leu Thr
            340                 345                 350
Ala Leu Asn Lys Ile Phe Ala Glu Gln Gly Val Asn Ile Ala Ala Gln
        355                 360                 365
Tyr Leu Gln Thr Ser Ala Gln Met Gly Tyr Val Val Ile Asp Ile Glu
    370                 375                 380
Ala Asp Glu Asp Val Ala Glu Lys Ala Leu Gln Ala Met Lys Ala Ile
385                 390                 395                 400
Pro Gly Thr Ile Arg Ala Arg Leu Leu Tyr
                405                 410

<210> SEQ ID NO 19
<211> LENGTH: 1053
<212> TYPE: DNA
<213> ORGANISM: Escherichia coli
<220> FEATURE:
<221> NAME/KEY: CDS
<222> LOCATION: (1)..(1053)

<400> SEQUENCE: 19 atg aat tat cag aac gac gat tta cgc atc aaa gaa atc aaa gag tta       48
Met Asn Tyr Gln Asn Asp Asp Leu Arg Ile Lys Glu Ile Lys Glu Leu
1               5                   10                  15 ctt cct cct gtc gca ttg ctg gaa aaa ttc ccc gct act gaa aat gcc       96
Leu Pro Pro Val Ala Leu Leu Glu Lys Phe Pro Ala Thr Glu Asn Ala
            20                  25                  30 gcg aat acg gtt gcc cat gcc cga aaa gcg atc cat aag atc ctg aaa      144
```

```
                Ala Asn Thr Val Ala His Ala Arg Lys Ala Ile His Lys Ile Leu Lys
                        35                  40                  45 ggt aat gat gat cgc ctg ttg gtt gtg att ggc cca tgc tca att cat                 192
Gly Asn Asp Asp Arg Leu Leu Val Val Ile Gly Pro Cys Ser Ile His
         50                  55                  60 gat cct gtc gcg gca aaa gag tat gcc act cgc ttg ctg gcg ctg cgt                 240
Asp Pro Val Ala Ala Lys Glu Tyr Ala Thr Arg Leu Leu Ala Leu Arg
65                  70                  75                  80 gaa gag ctg aaa gat gag ctg gaa atc gta atg cgc gtc tat ttt gaa                 288
Glu Glu Leu Lys Asp Glu Leu Glu Ile Val Met Arg Val Tyr Phe Glu
                85                  90                  95 aag ccg cgt acc acg gtg ggc tgg aaa ggg ctg att aac gat ccg cat                 336
Lys Pro Arg Thr Thr Val Gly Trp Lys Gly Leu Ile Asn Asp Pro His
            100                 105                 110 atg gat aat agc ttc cag atc aac gac ggt ctg cgt ata gcc cgt aaa                 384
Met Asp Asn Ser Phe Gln Ile Asn Asp Gly Leu Arg Ile Ala Arg Lys
        115                 120                 125 ttg ctg ctt gat att aac gac agc ggt ctg cca gcg gca ggt gag ttt                 432
Leu Leu Leu Asp Ile Asn Asp Ser Gly Leu Pro Ala Ala Gly Glu Phe
    130                 135                 140 ctc gat atg atc acc cca caa tat ctc gct gac ctg atg agc tgg ggc                 480
Leu Asp Met Ile Thr Pro Gln Tyr Leu Ala Asp Leu Met Ser Trp Gly
145                 150                 155                 160 gca att ggc gca cgt acc acc gaa tcg cag gtg cac cgc gaa ctg gca                 528
Ala Ile Gly Ala Arg Thr Thr Glu Ser Gln Val His Arg Glu Leu Ala
                165                 170                 175 tca ggg ctt tct tgt ccg gtc ggc ttc aaa aat ggc acc gac ggt acg                 576
Ser Gly Leu Ser Cys Pro Val Gly Phe Lys Asn Gly Thr Asp Gly Thr
            180                 185                 190 att aaa gtg gct atc gat gcc att aat gcc gcc ggt gcg ccg cac tgc                 624
Ile Lys Val Ala Ile Asp Ala Ile Asn Ala Ala Gly Ala Pro His Cys
        195                 200                 205 ttc ctg tcc gta acg aaa tgg ggg cat tcg gcg att gtg aat acc agc                 672
Phe Leu Ser Val Thr Lys Trp Gly His Ser Ala Ile Val Asn Thr Ser
    210                 215                 220 ggt aac ggc gat tgc cat atc att ctg cgc ggc ggt aaa gag cct aac                 720
Gly Asn Gly Asp Cys His Ile Ile Leu Arg Gly Gly Lys Glu Pro Asn
225                 230                 235                 240 tac agc gcg aag cac gtt gct gaa gtg aaa gaa ggg ctg aac aaa gca                 768
Tyr Ser Ala Lys His Val Ala Glu Val Lys Glu Gly Leu Asn Lys Ala
                245                 250                 255 ggc ctg cca gca cag gtg atg atc gat ttc agc cat gct aac tcg tcc                 816
Gly Leu Pro Ala Gln Val Met Ile Asp Phe Ser His Ala Asn Ser Ser
            260                 265                 270 aaa caa ttc aaa aag cag atg gat gtt tgt gct gac gtt tgc cag cag                 864
Lys Gln Phe Lys Lys Gln Met Asp Val Cys Ala Asp Val Cys Gln Gln
        275                 280                 285 att gcc ggt ggc gaa aag gcc att att ggc gtg atg gtg gaa agc cat                 912
Ile Ala Gly Gly Glu Lys Ala Ile Ile Gly Val Met Val Glu Ser His
    290                 295                 300 ctg gtg gaa ggc aat cag agc ctc gag agc ggg gag ccg ctg gcc tac                 960
Leu Val Glu Gly Asn Gln Ser Leu Glu Ser Gly Glu Pro Leu Ala Tyr
305                 310                 315                 320 ggt aag agc atc acc gat gcc tgc atc ggc tgg gaa gat acc gat gct                 1008
Gly Lys Ser Ile Thr Asp Ala Cys Ile Gly Trp Glu Asp Thr Asp Ala
                325                 330                 335 ctg tta cgt caa ctg gcg aat gca gta aaa gcg cgt cgc ggg taa                     1053
Leu Leu Arg Gln Leu Ala Asn Ala Val Lys Ala Arg Arg Gly
            340                 345                 350
```

```
<210> SEQ ID NO 20
<211> LENGTH: 350
<212> TYPE: PRT
<213> ORGANISM: Escherichia coli

<400> SEQUENCE: 20

Met Asn Tyr Gln Asn Asp Asp Leu Arg Ile Lys Glu Ile Lys Glu Leu
 1               5                  10                  15

Leu Pro Pro Val Ala Leu Leu Glu Lys Phe Pro Ala Thr Glu Asn Ala
                20                  25                  30

Ala Asn Thr Val Ala His Ala Arg Lys Ala Ile His Lys Ile Leu Lys
            35                  40                  45

Gly Asn Asp Asp Arg Leu Leu Val Val Ile Gly Pro Cys Ser Ile His
 50                  55                  60

Asp Pro Val Ala Ala Lys Glu Tyr Ala Thr Arg Leu Leu Ala Leu Arg
 65                  70                  75                  80

Glu Glu Leu Lys Asp Glu Leu Glu Ile Val Met Arg Val Tyr Phe Glu
                85                  90                  95

Lys Pro Arg Thr Thr Val Gly Trp Lys Gly Leu Ile Asn Asp Pro His
                100                 105                 110

Met Asp Asn Ser Phe Gln Ile Asn Asp Gly Leu Arg Ile Ala Arg Lys
            115                 120                 125

Leu Leu Leu Asp Ile Asn Asp Ser Gly Leu Pro Ala Ala Gly Glu Phe
130                 135                 140

Leu Asp Met Ile Thr Pro Gln Tyr Leu Ala Asp Leu Met Ser Trp Gly
145                 150                 155                 160

Ala Ile Gly Ala Arg Thr Thr Glu Ser Gln Val His Arg Glu Leu Ala
                165                 170                 175

Ser Gly Leu Ser Cys Pro Val Gly Phe Lys Asn Gly Thr Asp Gly Thr
            180                 185                 190

Ile Lys Val Ala Ile Asp Ala Ile Asn Ala Ala Gly Ala Pro His Cys
        195                 200                 205

Phe Leu Ser Val Thr Lys Trp Gly His Ser Ala Ile Val Asn Thr Ser
210                 215                 220

Gly Asn Gly Asp Cys His Ile Ile Leu Arg Gly Gly Lys Glu Pro Asn
225                 230                 235                 240

Tyr Ser Ala Lys His Val Ala Glu Val Lys Glu Gly Leu Asn Lys Ala
                245                 250                 255

Gly Leu Pro Ala Gln Val Met Ile Asp Phe Ser His Ala Asn Ser Ser
            260                 265                 270

Lys Gln Phe Lys Lys Gln Met Asp Val Cys Ala Asp Val Cys Gln Gln
        275                 280                 285

Ile Ala Gly Gly Glu Lys Ala Ile Ile Gly Val Met Val Glu Ser His
    290                 295                 300

Leu Val Glu Gly Asn Gln Ser Leu Glu Ser Gly Glu Pro Leu Ala Tyr
305                 310                 315                 320

Gly Lys Ser Ile Thr Asp Ala Cys Ile Gly Trp Glu Asp Thr Asp Ala
                325                 330                 335

Leu Leu Arg Gln Leu Ala Asn Ala Val Lys Ala Arg Arg Gly
            340                 345                 350

<210> SEQ ID NO 21
<211> LENGTH: 2438
<212> TYPE: DNA
<213> ORGANISM: Artificial
```

<220> FEATURE:
<223> OTHER INFORMATION: Ptac-ideal->AroG4-SerA5

<400> SEQUENCE: 21

```
gtggaattgt gagcgctcac aattccacac ggatctctcc ccatccccct gttgacaatt      60
aatcatcggc tcgtataatg tgtggaattg tgagcggata acaatttcac acaggatcta     120
gaaggagcag acatgaatta tcagaacgac gatttacgca tcaaagaaat caaagagtta     180
cttcctcctg tcgcattgct ggaaaaattc cccgctactg aaaatgccgc gaatacggtt     240
gcccatgccc gaaaagcgat ccataagatc ctgaaaggta tgatgatcg cctgttggtt      300
gtgattggcc catgctcaat tcatgatcct gtcgcggcaa aagagtatgc cactcgcttg     360
ctggcgctgc gtgaagagct gaaagatgag ctggaaatcg taatgcgcgt ctattttgaa     420
aagccgcgta ccacggtggg ctggaaaggg ctgattaacg atccgcatat ggataatagc     480
ttccagatca cgacggtct gcgtatagcc cgtaaattgc tgcttgatat taacgacagc      540
ggtctgccag cggcaggtga gtttctcgat atgatcaccc tacaatatct cgctgacctg     600
atgagctggg gcgcaattgg cgcacgtacc accgaatcgc aggtgcaccg cgaactggca     660
tcagggcttt cttgtccggt cggcttcaaa aatggcaccg acggtacgat taaagtggct     720
atcgatgcca ttaatgccgc cggtgcgccg cactgcttcc tgtccgtaac gaaatggggg     780
cattcggcga ttgtgaatac cagcggtaac ggcgattgcc atatcattct gcgcggcggt     840
aaagagccta actacagcgc gaagcacgtt gctgaagtga agaagggct gaacaaagca      900
ggcctgccag cacaggtgat gatcgatttc agccatgcta actcgtccaa acaattcaaa     960
aagcagatgg atgtttgtgc tgacgtttgc cagcagattg ccggtggcga aaaggccatt    1020
attggcgtga tggtggaaag ccatctggtg aaggcaatc agagcctcga gagcggggag     1080
ccgctggcct acggtaagag catcaccgat gcctgcatcg gctgggaaga taccgatgct    1140
ctgttacgtc aactggcgaa tgcagtaaaa gcgcgtcgcg gtaacccgg gaagacagga    1200
ttgggtaaat ggcaaaggta tcgctggaga aagacaagat taagtttctg ctggtagaag    1260
gcgtgcacca aaaggcgctg aaaagccttc gtgcagctgg ttacaccaac atcgaatttc    1320
acaaaggcgc gctggatgat gaacaattaa agaatccat ccgcgatgcc cacttcatcg     1380
gcctgcgatc ccgtacccat ctgactgaag acgtgatcaa cgccgcagaa aaactggtcg    1440
ctattggctg tttctgtatc ggaacaaacc aggttgatct ggatgcggcg caaagcgcg     1500
ggatcccggt atttaacgca ccgttctcaa atacgcgctc tgttgcggag ctggtgattg    1560
gcgaactgct gctgctattg cgcggcgtgc cggaagccaa tgctaaagcg caccgtggcg    1620
tgtggaacaa actggcggcg ggttcttttg aagcgcgcgg caaaaagctg ggtatcatcg    1680
gctacggtca tattggtacg caattgggca ttctggctga atcgctggga atgtatgttt    1740
acttttatga tattgaaaat aaactgccgc tgggcaacgc cactcaggta cagcatcttt    1800
ctgacctgct gaatatgagc gatgtggtga tctgcatgt accagagaat ccgtccacca     1860
aaaatatgat gggcgcgaaa gaatttcac taatgaagcc cggctcgctg ctgattaatg     1920
cttcgcgcgg tactgtggtg gatattccgg cgctgtgtga tgcgctggcg agcaaacatc    1980
tggcggggc ggcaatcgac gtattcccga cggaaccggc gaccaatagc gatccattta     2040
cctctccgct gtgtgaattc gacaacgtcc ttctgacgcc acacattggc ggttcgactc    2100
aggaagcgca ggagaatatc ggcctggaag ttgcgggtaa attgatcaag tattctgaca    2160
atggctcaac gctctctgcg gtgaacttcc cggaagtctc gctgccactg cacggtgggc    2220
```

-continued

```
gtcgtctgat gcacatccac gaaaaccgtc cgggcgtgct aactgcgctg aacaaaatct    2280
tcgccgagca gggcgtcaac atcgccgcgc aatatctgca aacttccgcc cagatgggtt    2340
atgtggttat tgatattgaa gccgacgaag acgttgccga aaaagcgctg caggcaatga    2400
aagctattcc gggtaccatt cgcgcccgtc tgctgtaa                            2438
```

METHOD FOR PRODUCING AN L-AMINO ACID USING A BACTERIUM OF THE ENTEROBACTERIACEAE FAMILY WITH ATTENUATED EXPRESSION OF THE YDIN GENE OR THE YDIB GENE OR COMBINATION THEREOF

This application is a continuation of PCT/JP2007/066322, filed Aug. 16, 2007, which claims priority under 35 U.S.C. §119 to Russian Patent Application No. 2006129690, filed on Aug. 16, 2006, which are incorporated in their entireties by reference. The Sequence Listing in electronic format filed herewith is also hereby incorporated by reference in its entirety (File Name: US-384_Seq_List; File Size: 39 KB; Date Created: Feb. 17, 2009).

BACKGROUND OF THE INVENTION

1. Field of the Invention

The present invention relates to the microbiological industry, and specifically to a method for producing an aromatic L-amino acid using a bacterium of the Enterobacteriaceae family which has been modified to attenuate expression of the ydiN gene, the ydiB gene, or both.

2. Brief Description of the Related Art

Conventionally, L-amino acids are industrially produced by fermentation utilizing strains of microorganisms obtained from natural sources, or mutants thereof. Typically, the microorganisms are modified to enhance production yields of L-amino acids.

Many techniques to enhance L-amino acid production yields have been reported, including by transforming microorganisms with recombinant DNA (see, for example, U.S. Pat. No. 4,278,765). Other techniques for enhancing production yields include increasing the activities of enzymes involved in amino acid biosynthesis and/or desensitizing the target enzymes of the feedback inhibition by the resulting L-amino acid (see, for example, WO 95/16042, or U.S. Pat. Nos. 4,346,170, 5,661,012, and 6,040,160).

Another way to enhance L-amino acid production yields is to attenuate expression of a gene or several genes involved in degradation of the target L-amino acid, genes which divert the precursors of the target L-amino acid from the L-amino acid biosynthetic pathway, genes involved in the redistribution of carbon, nitrogen, and phosphate fluxes, genes coding for toxins, etc.

Shikimate dehydrogenase catalyzes the fourth step of the shikimate pathway, which is the essential route for the biosynthesis of aromatic compounds in plants and microorganisms. *Escherichia coli* expresses two shikimate dehydrogenase paralogs, the NADP-specific AroE and a putative enzyme YdiB. YdiB is characterized as a dual specificity quinate/shikimate dehydrogenase that utilizes either NAD or NADP as a cofactor. The structures of AroE and YdiB with bound cofactors were determined at 1.5 and 2.5 Å resolution, respectively. Both enzymes display a similar structure with two alpha/beta domains separated by a wide cleft. Comparison of their dinucleotide-binding domains reveals the molecular basis for cofactor specificity. Independent molecules display conformational flexibility which suggests that a switch between the open and closed conformation occurs upon substrate binding. Sequence analysis and structural comparison led to a proposal for the catalytic machinery and a model for 3-dehydroshikimate recognition. (Michel G., et al., J Biol. Chem. 23; 278(21):19463-72 (2003)).

The *Escherichia coli* YdiB protein, an orthologue of shikimate 5-dehydrogenase, catalyzes the reduction of 3-dehydroshikimate to shikimate as part of the shikimate pathway, which is absent in mammals but required for the de novo synthesis of aromatic amino acids, quinones, and folate in many other organisms. In this context, the shikimate pathway has been selected as a target for the development of antimicrobial agents. The crystal structure of YdiB shows that the promoter contains two alpha/beta domains connected by two alpha-helices, with the N-terminal domain being novel and the C-terminal domain being a Rossmann fold. The $NAD^+$ cofactor, which co-purified with the enzyme, is bound to the Rossmann domain in an elongated fashion with the nicotinamide ring in the pro-R conformation. Its binding site contains several unusual features, including a cysteine residue opposite to the nicotinamide ring and a clamp-like structure over the ribose of the adenosine moiety formed by phenylalanine and lysine residues. The structure explains the specificity for NAD versus NADP in different members of the shikimate dehydrogenase family on the basis of variations in the amino acid identity of several other residues in the vicinity of this ribose group. A cavity lined by residues that are 100% conserved among all shikimate dehydrogenases is found between the two domains of YdiB, in close proximity to the hydride acceptor site on the nicotinamide ring. Shikimate was modeled into this site in a geometry such that all of its heteroatoms form high quality hydrogen bonds with these invariant residues. Their strong conservation among all the orthologues supports the possibility of developing broad spectrum inhibitors of this enzyme. The nature and disposition of the active site residues suggest a novel reaction mechanism in which an aspartate acts as the general acid/base catalyst during the hydride transfer reaction (Benach J., et. al., J Biol. Chem. 23; 278(21):19176-82 (2003)).

When shikimic acid is produced by genetically modified *Escherichia coli*, it has previously been found that carbon-rich conditions (e.g. phosphate-limiting) favor production of shikimic acid over shikimate pathway by-products, whereas the situation is the opposite under carbon-(glucose-) limited conditions. Gene expression patterns of the shikimate producing strain W3110.shik1 (W3110 with an aroL deletion and plasmid-overexpressed aroF) and the wild-type strain W3110 grown under carbon- and phosphate-limited (carbon-rich) chemostat conditions (D=0.23 h(−1)) were analyzed. The study suggests that the by-product formation when carbon is limited is explained by a set of upregulated genes coupled to the shikimate pathway. The genes ydiB, aroD, and ydiN were strongly induced only in carbon-limited W3110.shik1. Compared to W3110, the 1 g(2)-fold changes were: 6.25 (ydiB), 3.93 (aroD), and 8.18 (ydiN). In addition, the transcriptome analysis revealed a large change in the gene expression when comparing phosphate-limited conditions to carbon-limited, which to a large part could be explained by anabolic-catabolic uncoupling, which is present under phosphate-limited but not under carbon-limited conditions. Interestingly, there was also a larger difference between the two strains under carbon-limited conditions than under phosphate-limited. The reason for this difference is interpreted as a starvation for aromatic amino acids under carbon-limited conditions, which is relieved under phosphate-limited conditions due to an upregulation of aroK and aroA (Johansson L. and Liden G., J. Biotechnol. In Press, Corrected Proof, Available online 17 May 2006).

But currently, there have been no reports of attenuating expression of the ydiN gene or the ydiB gene or the combination thereof for the purpose of producing L-amino acids.

SUMMARY OF THE INVENTION

Aspects of the present invention include enhancing the productivity of aromatic L-amino acid-producing strains and providing a method for producing L-amino acids using these strains.

The above aspects were achieved by finding that attenuating expression of the ydiN gene, the ydiB gene, or both can enhance production of aromatic L-amino acids, such as L-phenylalanine, L-tyrosine and L-tryptophan.

The present invention provides a bacterium of the Enterobacteriaceae family which has an increased ability to produce aromatic L-amino acids, such as L-phenylalanine, L-tyrosine, and L-tryptophan.

It is an aspect of the present invention to provide an aromatic L-amino acid-producing bacterium of the Enterobacteriaceae family, wherein the bacterium has been modified to attenuate expression of a gene selected from the group consisting of ydiN, ydiB, or both.

It is a further aspect of the present invention to provide the bacterium as described above, wherein said expression is attenuated by inactivating the ydiN gene, the ydiB gene, or both genes.

It is a further aspect of the present invention to provide the bacterium as described above, wherein the bacterium belongs to the genus *Escherichia*.

It is a further aspect of the present invention to provide the bacterium as described above, wherein the bacterium belongs to the genus *Pantoea*.

It is a further aspect of the present invention to provide the bacterium as described above, wherein said aromatic L-amino acid is selected from the group consisting of L-phenylalanine, L-tyrosine, and L-tryptophan.

It is a further aspect of the present invention to provide a method for producing an aromatic L-amino acid comprising:

cultivating the bacterium as described above in a medium, and collecting said aromatic L-amino acid from the medium.

It is a further aspect of the present invention to provide the method as described above, wherein said aromatic L-amino acid is selected from the group consisting of L-phenylalanine, L-tyrosine, and L-tryptophan.

It is a further aspect of the present invention to provide a method for producing a lower alkyl ester of α-L-aspartyl-L-phenylalanine, comprising cultivating the bacterium as described above in a culture medium, and synthesizing the lower alkyl ester of α-L-aspartyl-L-phenylalanine from aspartic acid or derivative thereof, and the L-phenylalanine which is produced by the bacterium, wherein said bacterium is able to produce L-phenylalanine.

It is a further aspect of the present invention to provide the method as described above, further comprising esterifying L-phenylalanine to generate a lower alkyl ester of L-phenylalanine, condensing the lower alkyl ester of L-phenylalanine with an aspartic acid derivative, wherein the derivative is N-acyl-L-aspartic anhydride, separating the lower alkyl ester of N-acyl-α-L-aspartyl-L-phenylalanine from the reaction mixture, and hydrogenating the lower alkyl ester of N-acyl-α-L-aspartyl-L-phenylalanine to generate the lower alkyl ester of α-L-aspartyl-L-phenylalanine.

The present invention is described in detail below.

DETAILED DESCRIPTION OF THE PREFERRED EMBODIMENTS

1. Bacterium

Figure 1:
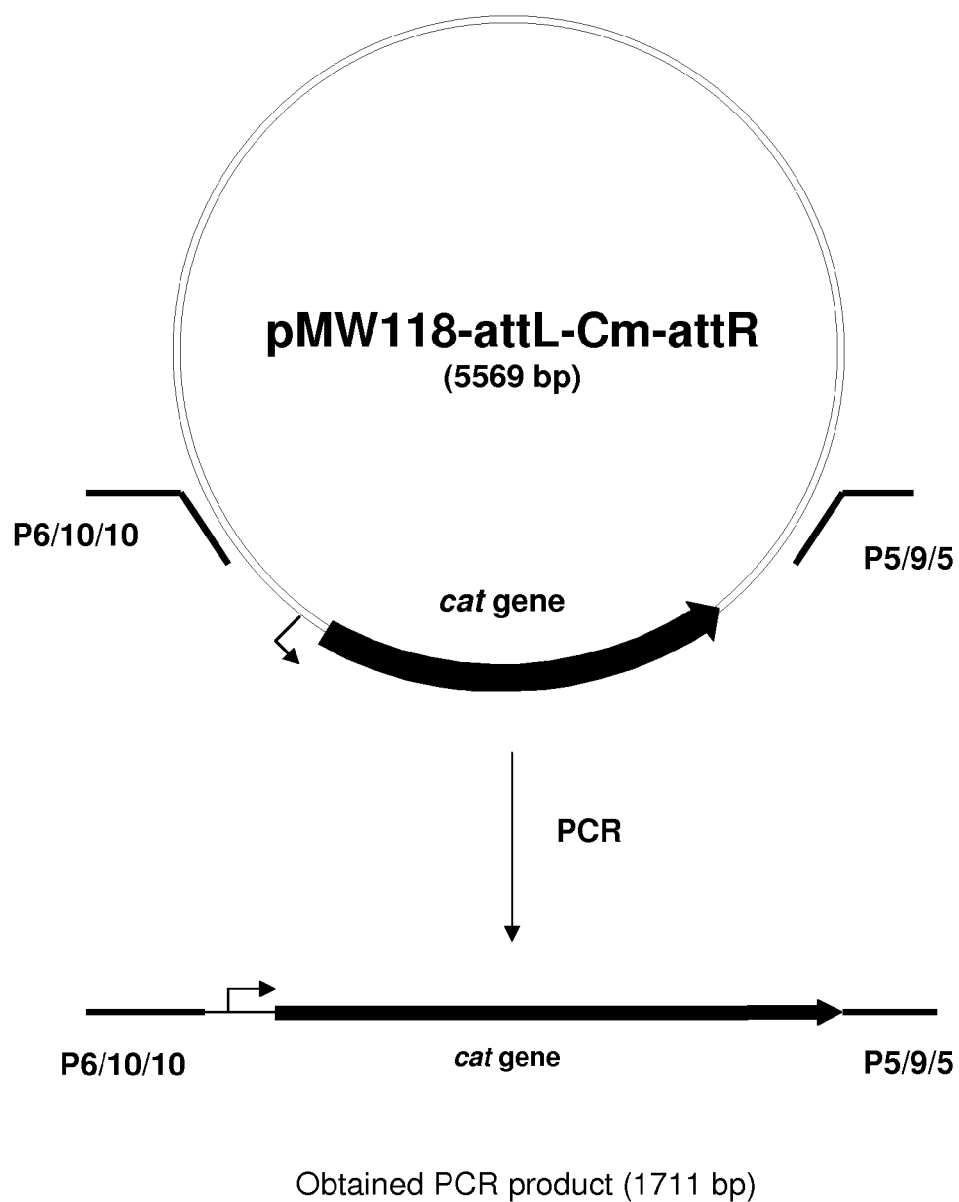
FIG. 1 shows the relative positions of primers P5/9/5 and P6/10/10 on plasmid pMW118-attL-Cm-attR. This plasmid is used as a template for PCR amplification of the cat gene.

The bacterium is an aromatic L-amino acid-producing bacterium of the Enterobacteriaceae family, wherein the bacterium has been modified to attenuate expression of the ydiN gene, the ydiB gene, or both.

The phrase "aromatic L-amino acid-producing bacterium" means a bacterium which has an ability to produce and secrete an aromatic L-amino acid into a medium, when the bacterium is cultured in the medium.

The term "aromatic L-amino acid-producing bacterium" also means a bacterium which is able to produce and cause accumulation of an aromatic L-amino acid in a culture medium in an amount larger than a wild-type, a parental strain, or an unmodified strain of the bacterium, for example, *E. coli*, such as *E. coli* K-12, and preferably means that the bacterium is able to cause accumulation in a medium of an amount not less than 0.5 g/L, more preferably not less than 1.0 g/L, of the target L-amino acid. The term "aromatic L-amino acid" includes, at least, L-phenylalanine, L-tyrosine and L-tryptophan.

The Enterobacteriaceae family includes bacteria belonging to the genera *Escherichia, Enterobacter, Erwinia, Klebsiella, Pantoea, Photorhabdus, Providencia, Salmonella, Serratia, Shigella, Morganella, Yersinia*, etc. Specifically, bacteria classified into the Enterobacteriaceae family according to the taxonomy used by the NCBI (National Center for Biotechnology Information) database (http://www.ncbi.nlm.nih.gov/Taxonomy/Browser/wwwtax.cgi?id=91347) can be used. A bacterium belonging to the genus *Escherichia* or *Pantoea* is preferred.

The phrase "a bacterium belonging to the genus *Escherichia*" means that the bacterium is classified into the genus *Escherichia* according to the classification known to a person skilled in the art of microbiology. Examples of a bacterium belonging to the genus *Escherichia* include, but are not limited to, *Escherichia coli* (*E. coli*).

The bacterium belonging to the genus *Escherichia* is not particularly limited, however, for example, bacteria described by Neidhardt, F. C. et al. (*Escherichia coli* and *Salmonella typhimurium*, American Society for Microbiology, Washington D.C., 1208, Table 1) are encompassed.

The phrase "a bacterium belonging to the genus *Pantoea*" means that the bacterium is classified as the genus *Pantoea* according to the classification known to a person skilled in the art of microbiology. Some species of *Enterobacter agglomerans* have been recently re-classified into *Pantoea agglomerans, Pantoea ananatis, Pantoea stewartii* or the like, based on the nucleotide sequence analysis of 16S rRNA, etc. (Int. J. Syst. Bacteriol., 43, 162-173 (1993)).

The phrase "bacterium has been modified to attenuate expression of the ydiN gene, the ydiB gene, or both" means that the bacterium has been modified in such a way that the modified bacterium contains a reduced amount of the YdiN protein, the ydiB protein, or both as compared with an unmodified bacterium, or is unable to synthesize the YdiN protein, the ydiB protein, or both.

The phrase "inactivation of the ydiN gene, the ydiB gene, or both" means that the modified gene encodes a completely non-functional protein. It is also possible that the modified DNA region is unable to naturally express the gene due to a deletion of a part of the gene, shifting of the reading frame of the gene, introduction of missense/nonsense mutation(s), or modification of an adjacent region of the gene, including sequences controlling gene expression, such as a promoter, enhancer, attenuator, ribosome-binding site, etc.

The presence or absence of the ydiN gene and/or the ydiB gene in the chromosome of a bacterium can be detected by well-known methods, including PCR, Southern blotting, and the like. In addition, the expression levels of the genes can be estimated by measuring the amounts of mRNA transcribed from the genes using various known methods including Northern blotting, quantitative RT-PCR, and the like. The amounts or molecular weights of the proteins coded by the genes can be measured by known methods including SDS-PAGE followed by an immunoblotting assay (Western blotting analysis), and the like.

The ydiN gene (synonyms: ECK1689, b1691) encodes the YdiN protein (synonym: B1691). The ydiN gene (nucleotides in positions 1,770,536 to 1,771,801; GenBank accession no. NC_000913.2; gi: 49175990) is located between the ydiM ORF and the ydiB gene on the chromosome of E. coli K-12. The nucleotide sequence of the ydiN gene and the amino acid sequence of YdiN encoded by the ydiN gene are shown in SEQ ID NO: 1 and SEQ ID NO:2, respectively. The ydiB gene (synonyms: ECK1690, b1692) encodes the YdiB protein (synonym: B1692). The ydiB gene (nucleotides in positions 1,771,813 to 1,772,679; GenBank accession no. NC_000913.2; gi: 49175990) is located between the ydiN gene and the aroD gene on the chromosome of E. coli K-12. The nucleotide sequence of the ydiB gene and the amino acid sequence of YdiB encoded by the ydiB gene are shown in SEQ ID NO: 3 and SEQ ID NO:4, respectively.

Since there may be some differences in DNA sequences between the genera or strains of the Enterobacteriaceae family, the gene to be inactivated on the chromosome is not limited to the genes shown in SEQ ID No:1 and SEQ ID No:3, but may include genes homologous to SEQ ID No:1 and SEQ ID No:3 which encode variant proteins of the YdiN and YdiB proteins. The phrase "variant proteins" means proteins which have changes in their sequence, whether the changes are deletions, insertions, additions, or substitutions of amino acids. The number of changes in the variant proteins depends on the position in the three dimensional structure of the protein or the type of amino acid residue to be changed. It may be 1 to 30, preferably 1 to 15, and more preferably 1 to 5 in SEQ ID NO: 2 and SEQ ID NO: 4. These changes are conservative mutations that preserve the function of the protein. In other words, these changes can occur in regions of the protein which are not critical for the three dimensional structure of the protein. This is because some amino acids have high homology to one another so the three dimensional structure is not affected by such a change. A conservative mutation is a mutation wherein substitution takes place mutually among Phe, Trp, Tyr, if the substitution site is an aromatic amino acid; among Leu, Ile, Val, if the substitution site is a hydrophobic amino acid; between Gln, Asn, if it is a polar amino acid; among Lys, Arg, His, if it is a basic amino acid; between Asp, Glu, if it is an acidic amino acid; and between Ser, Thr, if it is an amino acid having a hydroxyl group. Typical conservative mutations are conservative substitutions. Examples of conservative substitutions include substitution of Ser or Thr for Ala, substitution of Gln, His or Lys for Arg, substitution of Glu, Gln, Lys, His for Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. Substitutions, deletions, insertions, additions, or inversions and the like of the amino acids described above include naturally occurring mutations (mutant or variant) depending on differences in species, or individual differences of microorganisms that retain the ydiN or ydiB gene. Such a gene can be obtained by modifying the nucleotide sequence shown in SEQ ID NO: 1 or 3 using, for example, site-directed mutagenesis, so that the site-specific amino acid residue in the protein encoded includes substitutions, deletions, insertions, or additions.

Moreover, the protein variant encoded by the ydiN gene and ydiB gene may have a homology of not less than 80%, preferably not less than 90%, and most preferably not less than 95%, with respect to the entire amino acid sequence shown in SEQ ID NO. 2 and SEQ ID No:4, respectively. Activity of YdiB protein can be measured by the method described by Benach J., et. al. (J Biol. Chem. 23; 278(21): 19176-82 (2003)) or Michel G., et al. (J Biol. Chem. 23; 278(21):19463-72 (2003)).

Moreover, the ydiN gene and ydiB gene may be a variant which hybridizes with the nucleotide sequence shown in SEQ ID NO: 1 and SEQ ID No:3, or a probe which can be prepared from the nucleotide sequence under stringent conditions. "Stringent conditions" include those under which a specific hybrid, for example, a hybrid having homology of not less than 60%, preferably not less than 70%, more preferably not less than 80%, still more preferably not less than 90%, and most preferably not less than 95%, is formed and a non-specific hybrid, for example, a hybrid having homology lower than the above, is not formed. For example, stringent conditions are exemplified by washing one time or more, preferably two or three times at a salt concentration of 1×SSC, 0.1% SDS, preferably 0.1×SSC, 0.1% SDS at 60° C. Duration of washing depends on the type of membrane used for blotting and, as a rule, should be what is recommended by the manufacturer. For example, the recommended duration of washing for the Hybond™ N+ nylon membrane (Amersham) under stringent conditions is 15 minutes. Preferably, washing may be performed 2 to 3 times. The length of the probe may be suitably selected, depending on the hybridization conditions, and is usually 100 bp to 1 kbp.

Homology between two amino acid sequences can be determined using the well-known methods, for example, the computer program BLAST 2.0.

Expression of the ydiN gene, the ydiB gene, or both can be attenuated by introducing a mutation into the gene on the chromosome so that the intracellular amount of the protein encoded by the gene is decreased as compared to an unmodified strain. Such a mutation can be the insertion of a drug-resistance gene, or the deletion of a part of the gene or the entire gene (Qiu, Z. and Goodman, M. F., J. Biol. Chem., 272, 8611-8617 (1997); Kwon, D. H. et al, J. Antimicrob. Chemother., 46, 793-796 (2000)). Expression of the ydiN gene, the ydiB gene, or both can also be attenuated by modifying an expression regulating sequence such as the promoter, the Shine-Dalgarno (SD) sequence, etc. (WO95/34672, Carrier, T. A. and Keasling, J. D., Biotechnol Prog 15, 58-64 (1999)).

For example, the following methods may be employed to introduce a mutation by gene recombination. A mutant gene is prepared, and the bacterium to be modified is transformed with a DNA fragment containing the mutant gene. Then, the native gene on the chromosome is replaced with the mutant gene by homologous recombination, and the resulting strain is selected. Such gene replacement by homologous recombination can be conducted by employing a linear DNA, which is known as "Red-driven integration" (Datsenko, K. A. and Wanner, B. L., Proc. Natl. Acad. Sci. USA, 97, 12, p 6640-6645 (2000)), or by methods employing a plasmid containing a temperature-sensitive replication site (U.S. Pat. No. 6,303,383 or JP 05-007491A). Furthermore, the incorporation of a site-specific mutation by gene substitution using homologous recombination such as set forth above can also be conducted with a plasmid which is unable to replicate in the host.

Expression of the gene can also be attenuated by insertion of a transposon or an IS factor into the coding region of the gene (U.S. Pat. No. 5,175,107), or by conventional methods, such as mutagenesis with UV irradiation or nitrosoguanidine (N-methyl-N'-nitro-N-nitrosoguanidine).

Inactivation of the gene can also be performed by conventional methods, such as by mutagenesis with UV irradiation or nitrosoguanidine (N-methyl-N'-nitro-N-nitrosoguanidine), site-directed mutagenesis, gene disruption using homologous recombination, or/and insertion-deletion mutagenesis (Yu, D. et al., Proc. Natl. Acad. Sci. USA, 2000, 97:12: 5978-83 and Datsenko, K. A. and Wanner, B. L., Proc. Natl. Acad. Sci. USA, 2000, 97:12: 6640-45) also called "Red-driven integration".

The above description regarding variant proteins, gene inactivation, and other methods can be applied to other proteins, genes, and the breeding of bacteria described below. Methods for preparation of plasmid DNA, digestion and ligation of DNA, transformation, selection of an oligonucleotide as a primer, and the like may be ordinary methods well-known to one skilled in the art. These methods are described, for instance, in Sambrook, J., Fritsch, E. F., and Maniatis, T., "Molecular Cloning: A Laboratory Manual, Second Edition", Cold Spring Harbor Laboratory Press (1989).

Aromatic L-Amino Acid-Producing Bacteria

A bacterium which is modified to attenuate expression of the ydiN gene, the ydiB gene, or both is able to produce an aromatic L-amino acids.

The bacterium can be obtained by attenuating expression of the ydiN gene, the ydiB gene, or both in a bacterium which inherently has the ability to produce aromatic L-amino acids. Alternatively, the bacterium can be obtained by imparting the ability to produce aromatic L-amino acids to a bacterium already having the attenuated expression of the ydiN gene, the ydiB gene, or both.

L-tryptophan, L-phenylalanine, and L-tyrosine are all aromatic amino acids and share a common biosynthesis pathway. Examples of the genes encoding biosynthesis enzymes for these aromatic amino acids include deoxyarabino-heptulosonate phosphate synthase (aroG), 3-dehydroquinate synthase (aroB), shikimate dehydratase, shikimate kinase (aroL), 5-enolpyruvylshikimate-3-phosphate synthase (aroA), and chorismate synthase (aroC) (EP763127). Therefore, by placing multiple copies of the genes encoding these enzymes on a plasmid or genome, the aromatic amino acid-producing ability can be improved. It is known that these genes are controlled by the tyrosine repressor (tyrR), so the enzyme activity of an aromatic amino acid biosynthesis may also be increased by deleting the tyrR gene (see EP763127).

In order to enhance an aromatic amino acid productivity of a bacterium, biosynthesis of an amino acid other than the target aromatic amino acid may be attenuated. For example, when the target amino acid is L-tryptophan, biosynthetic pathways of L-phenylalanine and/or L-tyrosine may be attenuated (U.S. Pat. No. 4,371,614). Furthermore, 3-deoxy-D-arabinoheptulosonate-7-phosphate synthetase (DS) which endoded by aroF or aroG gene is subject to feedback inhibition by aromatic amino acids. Therefore, the bacterium may be modified so that the bacterium contains mutant DS which is not subject to the feedback inhibition. Such a mutant DS can be obtained, for example, by replacing L-aspartic acid at position 147 or L-serine at position 181 with other amino acids in aroF. In the case of aroG, mutant DS can be obtained, for example, by replacing aspartic acid at position 146, L-methionine at position 147, L-proline at position 150, or L-alanine at position 202 with other amino acids, or replacing L-methionine at position 157 and L-alanine at position 219 with other amino acids. An aromatic L-amino acid producing bacterium can be obtained by introducing a mutant gene which encodes such a mutant DS (EP0488424) to the bacterium. Especially, a mutant aroG gene (aroG4) in which L-proline at position 150 is replaced by L-leucine is preferred. The nucleotide sequence of the wild-type aroG gene and the amino acid sequence of DS encoded by the aroG gene are shown in SEQ ID NO: 19 and SEQ ID NO:20, respectively.

L-Phenylalanine-Producing Bacteria

Examples of parent strains which can be used to derive L-phenylalanine-producing bacteria include, but are not limited to, strains belonging to the genus *Escherichia*, such as *E. coli* AJ12739 (tyrA::Tn10, tyrR) (VKPM B-8197), *E. coli* HW1089 (ATCC 55371) harboring the mutant pheA34 gene (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407,952). Also, as a parent strain, *E. coli* K-12 [W3110 (tyrA)/pPHAB (FERM BP-3566), *E. coli* K-12 [W3110 (tyrA)/pPHAD] (FERM BP-12659), *E. coli* K-12 [W3110 (tyrA)/pPHATerm] (FERM BP-12662) and *E. coli* K-12 [W3110 (tyrA)/pBR-aroG4, pACMAB] named as AJ 12604 (FERM BP-3579) may be used (EP 488-424 B1). Furthermore, L-phenylalanine producing bacteria belonging to the genus *Escherichia* with an enhanced activity of the protein encoded by the yedA gene or the yddG gene may also be used (U.S. patent applications 2003/0148473 A1 and 2003/0157667 A1).

L-Tryptophan-Producing Bacteria

Examples of parent strains which can be used to derive the L-tryptophan-producing bacteria include, but are not limited to, strains belonging to the genus *Escherichia*, such as *E. coli* JP4735/pMU3028 (DSM10122) and JP6015/pMU91 (DSM10123) deficient in tryptophanyl-tRNA synthetase encoded by mutant trpS gene (U.S. Pat. No. 5,756,345), *E. coli* SV164 (pGH5).

*E. coli* SV164 (pGH5) having a serA allele encoding phosphoglycerate dehydrogenase which is not subject to feedback inhibition by serine and a trpE allele encoding anthranilate synthase which is not subject to feedback inhibition by tryptophan (U.S. Pat. No. 6,180,373). The nucleotide sequence of the wild-type serA gene and the amino acid sequence of phosphoglycerate dehydrogenase encoded by the serA gene are shown in SEQ ID NO: 17 and SEQ ID NO: 18, respectively.

According to the description in WO94/08031 (International Patent Unexamined Publication in Japanese (Kohyo) No. 7-507693), a trpE deficient strain, *Escherichia coli* KB862 (DSM7196), was introduced with a mutant gene coding for anthranilate synthase to which feedback inhibition was desensitized (also referred to as "desensitized AS" hereafter) to obtain *Escherichia coli* SV164 (trpE8). This SV164 strain was introduced with a plasmid pGH5 (described in WO94/08031) containing a serA5 gene coding for phosphoglycerate dehydrogenase to which feedback inhibition was desensitized (also referred to as "desensitized PGD" hereafter). The SV164/pGH5 strain has ability to produce tryptophan and serine (U.S. Pat. No. 7,045,320).

*Escherichia coli* KB862 was designated as AJ13828, and deposited at the National Institute of Bioscience and Human-Technology, Agency of Industrial Science and Technology (currently, National Institute of Advanced Industrial Science and Technology, International Patent Organism Depositary, Central 6, 1-1 Higashi 1-chome, Tsukuba-shi, Ibaraki-ken, 305-8566, Japan) as an international deposit on Dec. 21, 2000 under the provisions of the Budapest Treaty and received an accession number of FERM BP-7405.

*E. coli* AGX17 (pGX44) (NRRL B-12263) and AGX6 (pGX50)aroP (NRRL B-12264) deficient in the enzyme tryptophanase (U.S. Pat. No. 4,371,614); *E. coli* AGX17/pGX50, pACKG4-pps in which a phosphoenolpyruvate-producing ability is enhanced (WO9708333, U.S. Pat. No. 6,319,696), and the like. L-tryptophan-producing bacteria belonging to the genus *Escherichia* which have enhanced activity of the protein encoded by the yedA or yddG genes may also be used (U.S. patent applications 2003/0148473 A1 and 2003/0157667 A1).

Examples of parent strains which can be used to derive the L-tryptophan-producing bacteria also include strains in which one or more activities are enhanced of the following enzymes: anthranilate synthase (trpE), phosphoglycerate dehydrogenase (serA), and tryptophan synthase (trpAB). The anthranilate synthase and phosphoglycerate dehydrogenase are both subject to feedback inhibition by L-tryptophan and L-serine, therefore a mutation desensitizing the feedback inhibition may be introduced into these enzymes. Specific examples of strains having such a mutation include *E. coli* SV164 which harbors desensitized anthranilate synthase and a transformant strain obtained by introducing into the *E. coli* SV164 the plasmid pGH5 (WO 94/08031), which contains a mutant serA gene encoding feedback-desensitized phosphoglycerate dehydrogenase.

Examples of parent strains which can be used to derive the L-tryptophan-producing bacteria also include strains which have been transformed with the tryptophan operon containing a gene encoding desensitized anthranilate synthase (JP 57-71397 A, JP 62-244382 A, U.S. Pat. No. 4,371,614). Moreover, L-tryptophan-producing ability may be imparted by enhancing expression of a gene which encodes tryptophan synthase, among tryptophan operons (trpBA). Tryptophan synthase consists of α and β subunits which are encoded by the trpA and trpB genes, respectively. In addition, L-tryptophan-producing ability may be improved by enhancing expression of the isocitrate lyase-malate synthase operon (WO2005/103275).

Examples of parent strains which can be used to derive the L-tryptophan-producing bacteria also include strains which have been transformed with the operon containing a gene encoding feedback-desensitized phosphoglycerate dehydrogenase and a gene encoding feedback-desensitized 3-deoxy-D-arabinoheptulosonate-7-phosphate synthetase. Specific examples of such strains include an *E. coli* SV164($P_{tac\text{-}ideal} \rightarrow$aroG4-serA5), containing operon $P_{tac\text{-}ideal} \rightarrow$aroG4-serA5, integrated into chromosome at position 2.933.542 in expression cassette from the plasmid pMDV3-aroG4-serA5. The integrative plasmid pMDV3-aroG4-serA5 was constructed on the basis of integrative plasmid pMDV3 (Zimenkov D. et al., Biotechnology in Russia, 6, 1-22 (2004)). Two DNA fragments were cloned into pMDV3. The first fragment is the DNA fragment BglII-XbaI of plasmid pMW118-$P_{tac\text{-}ideal} \rightarrow$lacZ-ter_rrnB (Mashko S. et. al., Biotechnology in Russia, 5, 3-20 (2001)), containing promoter $P_{tac\text{-}ideal}$ ($O_{lac\text{-}ideal}$-$P_{tac}$/$O_{lac}$). The second one is the DNA fragment XbaI-EcoRI of polylinker from plasmid pMW118 (GenBank/EMBL accession number AB005475). Furthermore, the amplified DNA fragment containing aroG4 was cloned into the plasmid pAROG4 (Kikuchi Y. et. al., Appl. And Env. Microb., 761-2 (1997)), which was used as a template with primers P1 (SEQ ID NO: 5) and P2 (SEQ ID NO: 6) for PCR. These primers contained the recognition sites for XbaI and SmaI endonucleases respectively. The plasmid pAROG4 harbors the aroG4 gene encoding 3-deoxy-D-arabino-heptulosinate-7-phosphate (DAHP) synthase which is not subject to feedback inhibition by phenylalanine. The resulting plasmid pMDV-aroG4 was used as a vector for cloning the structural part of serA5. The amplified DNA fragment containing serA5 was obtained by PCR using the plasmid pGH5 (U.S. Pat. No. 6,180,373) as the template and primers P3 (SEQ ID NO: 7) and P4 (SEQ ID NO: 8). The plasmid pGH5 harbors the serA5 gene encoding phosphoglycerate dehydrogenase which is not subject to feedback inhibition by serine. This amplified fragment has the recognition site for SmaI endonuclease in the 5'-region of serA5 gene and the recognition sites for SalI, SphI, SacI endonucleases in the 3'-region of serA5 gene. This DNA fragment was cloned into plasmid pMDV-aroG4 using the recognition sites for SmaI and SacI endonucleases. The resulting integrative plasmid pMDV3-aroG4-serA5 contained operon $P_{tac\text{-}ideal} \rightarrow$aroG4-serA5.

2. Method of the Present Invention

The method of the present invention is a method for producing an aromatic L-amino acid by cultivating the bacterium of the present invention in a culture medium to produce and secrete the aromatic L-amino acid into the medium, and collecting the aromatic L-amino acid from the medium.

The cultivation, collection, and purification of an aromatic L-amino acid from the medium and the like may be performed in a manner similar to conventional fermentation methods wherein an amino acid is produced using a bacterium.

The chosen culture medium may be either a synthetic or natural medium, so long as it includes a carbon source and a nitrogen source and minerals and, if necessary, appropriate amounts of nutrients which the bacterium requires for growth. The carbon source may include various carbohydrates such as glucose and sucrose, and various organic acids. Depending on the mode of assimilation of the chosen microorganism, alcohol, including ethanol and glycerol, may be used. As the nitrogen source, various ammonium salts such as ammonia and ammonium sulfate, other nitrogen compounds such as amines, a natural nitrogen source such as peptone, soybean-hydrolysate, and digested fermentative microorganism can be used. As minerals, potassium monophosphate, magnesium sulfate, sodium chloride, ferrous sulfate, manganese sulfate, calcium chloride, and the like can be used. As vitamins, thiamine, yeast extract, and the like, can be used.

The cultivation is preferably performed under aerobic conditions, such as a shaking culture, or a stirring culture with aeration, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 5-day cultivation leads to accumulation of the target aromatic L-amino acid in the liquid medium.

After cultivation, solids such as cells can be removed from the liquid medium by centrifugation or membrane filtration, and then the aromatic L-amino acid can be collected and purified by ion-exchange, concentration, and/or crystallization methods. Phenylalanine produced by the method of the present invention may be used for, for example, producing lower alkyl ester of α-L-aspartyl-L-phenylalanine (also referred to as "aspartame"). That is, the method includes a method for producing a lower alkyl ester of α-L-aspartyl-L-phenylalanine by using L-phenylalanine as a raw material. The method includes synthesizing a lower alkyl ester of α-L-aspartyl-L-phenylalanine from L-phenylalanine produced by the method as described above and aspartic acid or its derivative. As a lower alkyl ester, methyl ester, ethyl ester and propyl ester, or the like can be mentioned.

In the method, a process for synthesizing a lower alkyl ester of α-L-aspartyl-L-phenylalanine from L-phenylalanine and aspartic acid or its derivative is not particularly limited and any conventional method can be applied so long as L-phenylalanine or its derivative can be used for the synthesis of the lower alkyl ester of α-L-aspartyl-L-phenylalanine. Concretely, for example, lower alkyl esters of α-L-aspartyl-L-phenylalanine may be produced by the following process (U.S. Pat. No. 3,786,039). L-phenylalanine is esterified to obtain a lower alkyl ester of L-phenylalanine. The L-phenylalanine alkyl ester is reacted with L-aspartic acid derivative of which an amino group and .beta.carboxyl group are protected and a carboxyl group is esterified to activate. The derivative includes N-acyl-L-aspartic anhydrides such as N-formyl-, N-carbobenzoxy-, or N-p-methoxycarbobenzoxy-L-aspartic anhydride. By the condensation reaction, a mixture of N-acyl-α-L-aspartyl-L-phenylalanine and N-acyl-β-L-aspartyl-L-phenylalanine is obtained. If the condensation reaction is performed in the presence of an organic acid of which acid dissociation constant at 37° C. is $10^{-4}$ or less, ratio of α form to β form in the mixture is increased (Japanese Patent Laid-Open Publication No. 51-113841). Then, the N-acyl-α-L-aspartyl-L-phenylalanine is separated from the mixture, followed by hydrogenating to obtain α-L-aspartyl-L-phenylalanine.

EXAMPLES

The present invention will be more concretely explained below with reference to the following non-limiting Examples.

Example 1

Construction of a Strain with an Inactivated ydiN Gene

1. Deletion of the ydiN Gene

The ydiN gene was deleted by the method initially developed by Datsenko, K. A. and Wanner, B. L. (Proc. Natl. Acad. Sci. USA, 2000, 97(12), 6640-6645) called "Red-driven integration". The DNA fragment containing the $Cm^R$ marker encoded by the cat gene was obtained by PCR, using the primers P5 (SEQ ID NO: 9) and P6 (SEQ ID NO: 10), and the pMW118-attL-Cm-attR plasmid as a template (WO 05/010175). Primer P5 contains both a region complementary to the 36-nt region located at the 5' end of the ydiN gene, -tt-nucleotides for preventing frame-shift and the 28-nt region complementary to the 3' end of the attR region. Primer P6 contains both a region complementary to the 36-nt region located at the 3' end of the ydiN gene, and the 28-nt region complementary to the 5' end of the attL region. Conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

An 1711-bp PCR product (FIG. 1) was obtained and purified in an agarose gel and was used for electroporation of the E. coli strain MG1655 (ATCC 700926), which contains the pKD46 plasmid which has a temperature-sensitive replication origin. The pKD46 plasmid (Datsenko, K. A. and Wanner, B. L., Proc. Natl. Acad. Sci. USA, 2000, 97:12:6640-45) includes a 2,154 nucleotide DNA fragment of phage λ (nucleotide positions 31088 to 33241, GenBank accession no. J02459), and contains genes of the λ Red homologous recombination system (γ, β, exo genes) under the control of the arabinose-inducible $P_{araB}$ promoter. The plasmid pKD46 is necessary for integration of the PCR product into the chromosome of strain MG1655. The strain MG1655 can be obtained from the American Type Culture Collection. (P.O. Box 1549 Manassas, Va. 20108, U.S.A.).

Electrocompetent cells were prepared as follows: E. coli MG1655/pKD46 was grown overnight at 30° C. in LB medium containing ampicillin (100 mg/l), and the culture was diluted 100 times with 5 ml of SOB medium (Sambrook et al, "Molecular Cloning: A Laboratory Manual, Second Edition", Cold Spring Harbor Laboratory Press, 1989) containing ampicillin and L-arabinose (1 mM). The cells were grown with aeration at 30° C. to an $OD_{600}$ of ≈0.6 and then were made electrocompetent by concentrating 100-fold and washing three times with ice-cold deionized $H_2O$. Electroporation was performed using 70 µl of cells and 100 ng of the PCR product. Cells after electroporation were incubated with 1 ml of SOC medium (Sambrook et al, "Molecular Cloning: A Laboratory Manual, Second Edition", Cold Spring Harbor Laboratory Press, 1989) at 37° C. for 2.5 hours and then were plated onto L-agar containing chloramphenicol (30 µg/ml) and grown at 37° C. to select $Cm^R$ recombinants. Then, to eliminate the pKD46 plasmid, two passages on L-agar with Cm at 42° C. were performed and the obtained colonies were tested for sensitivity to ampicillin.

2. Verification of the ydiN Gene Deletion by PCR

Figure 2:
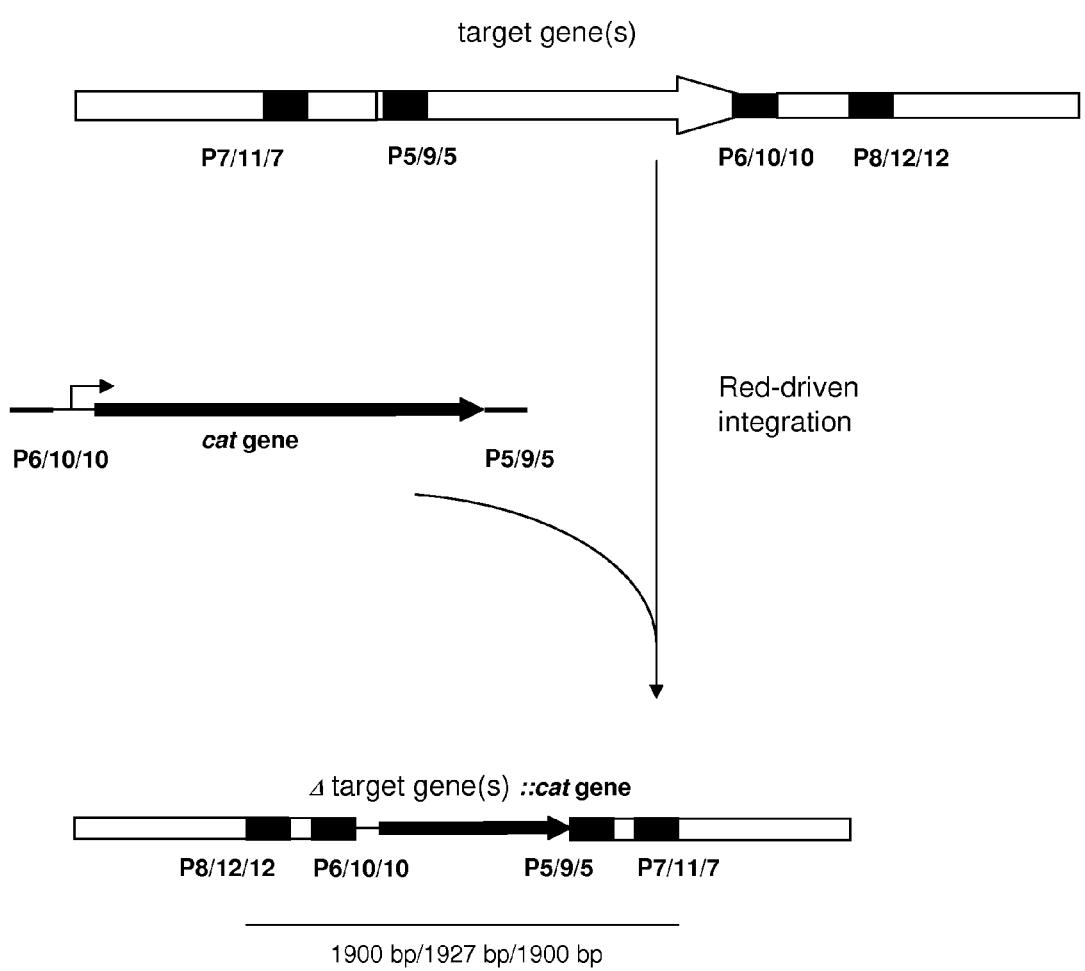
FIG. 2 shows the construction of the chromosomal DNA fragment containing the inactivated target gene(s).

The mutants having the ydiN gene deleted and marked with the Cm resistance gene were verified by PCR. Locus-specific primers P7 (SEQ ID NO: 11) and P8 (SEQ ID NO: 12) were used in PCR for the verification. Conditions for PCR verification were as follows: denaturation step for 3 min at 94° C.; profile for 30 cycles: 30 sec at 94° C., 30 sec at 54° C., 1 min at 72° C.; final step: 7 min at 72° C. The PCR product obtained using the parental ydiN+ strain MG1655 as a template, was 1461 bp in length. The PCR product obtained using the mutant strain as the template was 1900 bp in length (FIG. 2). The mutant strain was named MG1655 ΔydiN::cat.

Example 2

Production of L-phenylalanine by *E. coli* Strain AJ12739-ΔydiN

To test the effect of inactivation of the ydiN gene on L-phenylalanine production, DNA fragments from the chromosome of the above-described *E. coli* MG1655 ΔydiN::cat can be transferred to the phenylalanine-producing *E. coli* strain AJ12739 by P1 transduction (Miller, J. H. Experiments in Molecular Genetics, Cold Spring Harbor Lab. Press, 1972, Plainview, N.Y.) to obtain strain AJ12739-ΔydiN::cat. The strain AJ12739 has been deposited in the Russian National Collection of Industrial Microorganisms (VKPM) (Russia, 117545 Moscow, 1 Dorozhny proezd, 1) on Nov. 6, 2001 under accession no. VKPM B-8197 and then converted to a deposit under the Budapest Treaty on Aug. 23, 2002.

Furthermore, the Cm resistance gene (cat gene) can be eliminated from the chromosome of the strain AJ12739-ΔydiN::cat using the int-xis system. For that purpose, the AJ12739-ΔydiN::cat strain can be transformed with the pMWts-Int/Xis plasmid (WO 2005 010175). Transformant clones can be selected on the LB-medium containing 100 µg/ml of ampicillin. Plates can be incubated overnight at 30° C. Transformant clones can be cured from the cat gene by spreading the separate colonies at 37° C. (at that temperature repressor CIts is partially inactivated and transcription of the int/xis genes is derepressed) followed by selection of $Cm^S Ap^R$ variants. Elimination of the cat gene from the chromosome of the strain can be verified by PCR. Locus-specific primers P7 (SEQ ID NO: 11) and P8 (SEQ ID NO: 12) can be used in PCR for verification. Conditions for PCR verification can be as described above. The PCR product obtained in the reaction with cells not having the cat gene, should be 294 bp in length. Thus, the AJ12739-ΔydiN strain with the inactivated ydiN gene and eliminated cat gene can be obtained.

Both strains, AJ12739-ΔydiN and AJ12739, can each be cultivated at 37° C. for 18 hours in a nutrient broth, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC. The 10×15-cm TLC plates coated with 0.11-mm layers of Sorbfil silica gel containing no fluorescent indicator (Stock Company Sorbpolymer, Krasnodar, Russia) can be used. The Sorbfil plates can be developed with a mobile phase consisting of propan-2-ol: ethylacetate: 25% aqueous ammonia: water=40:40:7:16 (v/v). A solution of ninhydrin (2%) in acetone can be used as a visualizing reagent.

The composition of the fermentation medium (g/l) is as follows:

| | |
|---|---|
| Glucose | 40.0 |
| $(NH_4)_2SO_4$ | 16.0 |
| $K_2HPO_4$ | 0.1 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ is dry-heat sterilized at 180° C. for 2 hours. The pH is adjusted to 7.0.

Example 3

Production of L-tryptophan by *E. coli* Strain SV164 ($P_{tac-ideal}$→aroG4-serA5)-ΔydiN To test the effect of inactivation of the ydiN gene on L-tryptophan production, DNA fragments from the chromosome of the above-described *E. coli* strain MG1655 ΔydiN::cat can be transferred to the tryptophan-producing *E. coli* strain SV164 ($P_{tac-ideal}$→aroG4-serA5) by P1 transduction to obtain the strain SV164($P_{tac-ideal}$→aroG4-serA5)-ΔydiN::cat. The SV164 strain has the trpE allele encoding anthranilate synthase which is not subjected to feedback inhibition by tryptophan. The SV164 strain ($P_{tac-ideal}$→-aroG4-serA5) contains the $P_{tac-ideal}$→aroG4-serA5 operon, which is integrated into the chromosome at the 2.933.542 position in the expression cassette from the pMDV3-aroG4-serA5 plasmid. The nucleotide sequence of the $P_{tac-ideal}$→aroG4-serA5 operon is shown in SEQ ID NO: 21. The position of the genes in the operon is as follows: $P_{tac-ideal}$ (1 to 116), aroG4 (133 to 1185) and serA5 (1209 to 2438). In aroG4, L-proline at position 150 in the wild-type deoxyarabino-heptulosonate phosphate synthase (SEQ ID NO: 20) is replaced by L-leucine. In serA5, the tyrosine residue at position 410 in the wild-type phosphoglycerate dehydrogenase (SEQ ID NO: 18) is deleted.

Furthermore, the Cm resistance gene (cat gene) can be eliminated from the chromosome of the SV164 strain ($P_{tac-ideal}$→-aroG4-serA5)-ΔydiN::cat using the int-xis system. For that purpose, the SV164 strain ($P_{tac-ideal}$→aroG4-serA5)-ΔydiN::cat can be transformed with the pMWts-Int/Xis plasmid. Transformant clones can be selected on the LB-medium containing 100 µg/ml of ampicillin. Plates can be incubated overnight at 30° C. Transformant clones can be cured from the cat gene by spreading the separate colonies at 37° C. (at that temperature repressor CIts is partially inactivated and transcription of the int/xis genes is derepressed) followed by selection of $Cm^S Ap^R$ variants. Elimination of the cat gene from the chromosome of the strain can be verified by PCR. Locus-specific primers P7 (SEQ ID NO: 11) and P8 (SEQ ID NO: 12) can be used in PCR for verification. Conditions for PCR verification can be as described above. The PCR product obtained using the cells not having the eliminated cat gene, should be 294 bp in length. Thus, the SV164 strain ($P_{tac-ideal}$→aroG4-serA5)-ΔydiN with the inactivated ydiN gene and eliminated cat gene can be obtained.

Both of the SV164($P_{tac-ideal}$→aroG4-serA5)-ΔydiN and SV164($P_{tac-ideal}$→-aroG4-serA5) strains can each be cultivated with shaking at 32° C. for 18 hours in 3 ml of nutrient broth. The obtained cultures (0.3 ml each) can be inoculated into 3 ml of a fermentation medium in 20×200-mm test tubes, and cultivated at 32° C. for 72 hours with a rotary shaker at 250 rpm. After cultivation, the amount of tryptophan which accumulates in the medium can be determined by TLC as described in Example 2.

The fermentation medium components are listed in Table 1, but should be sterilized in separate groups (A, B, C, D, E, F, G and H), as shown, to avoid adverse interactions during sterilization.

TABLE 1

| Solutions | Component | Final concentration, g/l |
|---|---|---|
| A | KH$_2$PO$_4$ | 1.5 |
|   | NaCl | 0.5 |
|   | (NH$_4$)$_2$SO$_4$ | 15.0 |
|   | L-Methionine | 0.05 |
|   | L-Phenylalanine | 0.1 |
|   | L-Tyrosine | 0.1 |
|   | Mameno (total N) | 0.35 |
| B | Glucose | 40.0 |
|   | MgSO$_4$ 7H$_2$O | 0.3 |
| C | CaCl$_2$ 2H$_2$O | 14.7 |
| D | FeSO$_4$ 7H$_2$O | 0.075 |
| E | Na$_2$MoO$_4$ 2H$_2$O | 0.00015 |
|   | H$_3$BO$_3$ | 0.0025 |
|   | CoCl$_2$ 6H$_2$O | 0.0007 |
|   | CuSO$_4$ 5H$_2$O | 0.00025 |
|   | MnCl$_2$ 4H$_2$O | 0.0016 |
|   | ZnSO$_4$ 7H$_2$O | 0.0003 |
| F | Thiamine HCl | 0.005 |
| G | CaCO$_3$ | 30.0 |
| H | Pyridoxine | 0.03 |

The pH of solution A is adjusted to 7.1 with NH$_4$OH. Each group is sterilized separately, chilled, and then mixed together.

Example 4

Construction of a Strain with an Inactivated ydiB Gene

1. Deletion of the ydiB Gene

The ydiB gene was deleted by "Red-driven integration". The DNA fragment containing the Cm$^R$ marker encoded by the cat gene was obtained by PCR, using primers P9 (SEQ ID NO: 13) and P10 (SEQ ID NO: 14), and the pMW118-attL-Cm-attR plasmid as a template. Primer P9 contains both a region complementary to the 36-nt region located at the 5' end of the ydiB gene, -tt-nucleotides for preventing frame-shift and the 28-nt region complementary to the 3' end of the attR region. Primer P10 contains both a region complementary to the 36-nt region located at the 3' end of the ydiB gene and the 28-nt region complementary to the 5' end of the attL region. Conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

An 1711-bp PCR product (FIG. 1) was obtained and purified in agarose gel and was used for electroporation of the *E. coli* strain MG1655, which contains the plasmid pKD46 having a temperature-sensitive replication. The plasmid pKD46 is necessary for integration of the PCR product into the chromosome of strain MG1655.

Electrocompetent cells were prepared as follows: *E. coli* MG1655/pKD46 was grown overnight at 30° C. in LB medium containing ampicillin (100 mg/l), and the culture was diluted times with 5 ml of SOB medium containing ampicillin and L-arabinose (1 mM). The cells were grown with aeration at 30° C. to an OD$_{600}$ of ≈0.6 and then were made electrocompetent by concentrating 100-fold and washing three times with ice-cold deionized H$_2$O. Electroporation was performed using 70 µl of cells and ≈100 ng of the PCR product. Cells after electroporation were incubated with 1 ml of SOC medium at 37° C. for 2.5 hours and then were plated onto L-agar containing chloramphenicol (30 µg/ml) and grown at 37° C. to select Cm$^R$ recombinants. Then, to eliminate the pKD46 plasmid, two passages on L-agar with Cm at 42° C. were performed and the obtained colonies were tested for sensitivity to ampicillin.

2. Verification of the ydiB Gene Deletion by PCR

The mutants having the ydiB gene deleted and marked with the Cm resistance gene were verified by PCR. Locus-specific primers P11 (SEQ ID NO: 15) and P12 (SEQ ID NO: 16) were used in PCR for verification. Conditions for PCR verification were as follows: denaturation step for 3 min at 94° C.; profile for 30 cycles: 30 sec at 94° C., 30 sec at 54° C., 1 min at 72° C.; final step: 7 min at 72° C. The PCR product obtained using the parental ydiB$^+$ strain MG1655 as a template, was 1083 bp in length. The PCR product obtained using the mutant strain as the template was 1927 bp in length (FIG. 2). The mutant strain was named MG1655 ΔydiB::cat.

Example 5

Production of L-phenylalanine by *E. coli* Strain AJ12739-ΔydiB

To test the effect of inactivation of the ydiB gene on L-phenylalanine production, DNA fragments from the chromosome of the above-described *E. coli* MG1655 ΔydiB::cat can be transferred to the phenylalanine-producing *E. coli* strain AJ12739 by P1 transduction to obtain strain AJ12739-ΔydiB::cat.

Furthermore, the Cm resistance gene (cat gene) can be eliminated from the chromosome of the AJ12739-ΔydiB::cat strain using the int-xis system. For that purpose, the AJ12739-ΔydiB::cat strain can be transformed with the pMWts-Int/Xis plasmid. Transformant clones can be selected on LB-medium containing 100 µg/ml of ampicillin. Plates can be incubated overnight at 30° C. Transformant clones can be cured from the cat gene by spreading the separate colonies at 37° C. (at that temperature repressor CIts is partially inactivated and transcription of the int/xis genes is derepressed) followed by selection of Cm$^S$Ap$^R$ variants. Elimination of the cat gene from the chromosome of the strain can be verified by PCR. Locus-specific primers P11 (SEQ ID NO: 15) and P12 (SEQ ID NO: 16) can be used in PCR for verification. Conditions for PCR verification can be as described above. The PCR product obtained in reaction with cells not having the cat gene as a template, should be 321 bp in length. Thus, the AJ12739-ΔydiB strain with the inactivated ydiB gene and eliminated cat gene can be obtained.

Both of the AJ12739-ΔydiB and AJ12739 strains can each be cultivated at 37° C. for 18 hours in a nutrient broth, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC as described in Example 2.

The composition of the fermentation medium (g/l) is as follows:

| | |
|---|---|
| Glucose | 40.0 |
| (NH$_4$)$_2$SO$_4$ | 16.0 |
| K$_2$HPO$_4$ | 0.1 |
| MgSO$_4$ 7H$_2$O | 1.0 |
| FeSO$_4$•7H$_2$O | 0.01 |
| MnSO$_4$•5H$_2$O | 0.01 |
| Thiamine HCl | 0.0002 |
| Yeast extract | 2.0 |
| Tyrosine | 0.125 |
| CaCO$_3$ | 20.0 |

Glucose and magnesium sulfate are sterilized separately. CaCO$_3$ is dry-heat sterilized at 180° C. for 2 hours. The pH is adjusted to 7.0.

Example 6

Production of L-tryptophan by *E. coli* Strain SV164 (P$_{tac\text{-}ideal}$→aroG4-serA5)-ΔydiB To test the effect of inactivation of the ydiB gene on L-tryptophan production, DNA fragments from the chromosome of the above-described *E. coli* strain MG1655 ΔydiB::cat was transferred to the tryptophan-producing *E. coli* strain SV164 (P$_{tac\text{-}ideal}$→aroG4-serA5) by P1 transduction to obtain the strain SV164(P$_{tac\text{-}ideal}$→aroG4-serA5)-ΔydiB::cat.

Furthermore, the Cm resistance gene (cat gene) was eliminated from the chromosome of the SV164(P$_{tac\text{-}ideal}$→aroG4-serA5)-ΔydiB::cat strain using the int-xis system. For that purpose, the SV164(P$_{tac\text{-}ideal}$→-aroG4-serA5)-ΔydiB::cat strain was transformed with the pMWts-Int/Xis plasmid. Transformant clones were selected on the LB-medium containing 100 μg/ml of ampicillin. Plates were incubated overnight at 30° C. Transformant clones were cured from the cat gene by spreading the separate colonies at 37° C. (at that temperature repressor CIts is partially inactivated and transcription of the int/xis genes is derepressed) followed by selection of Cm$^S$Ap$^R$ variants. Elimination of the cat gene from the chromosome of the strain was verified by PCR. Locus-specific primers P11 (SEQ ID NO: 15) and P12 (SEQ ID NO: 16) were used in PCR for the verification. Conditions for PCR verification were as described above. The PCR product obtained using the cells not having the cat gene, should be 321 bp in length. Thus, the SV164(P$_{tac\text{-}ideal}$→aroG4-serA5)-ΔydiB strain with the inactivated ydiB gene and eliminated cat gene was obtained.

Both of the SV164(P$_{tac\text{-}ideal}$→aroG4-serA5)-ΔydiB and SV164(P$_{tac\text{-}ideal}$→aroG4-serA5) strains were each cultivated with shaking at 32° C. for 18 hours in 3 ml of nutrient broth. The obtained cultures (0.3 ml each) were inoculated into 3 ml of a fermentation medium in 20×200-mm test tubes, and cultivated at 32° C. for 50 hours with a rotary shaker at 250 rpm. It was determined that all glucose was utilized at that moment. After cultivation, the amount of tryptophan which accumulates in the medium was determined by TLC as described in Example 2. Results of at least three independent fermentations are presented in the Table 2. As it is seen, inactivation of ydiB gene increases tryptophan production.

The fermentation medium components are listed in Table 1, but should be sterilized in separate groups (A, B, C, D, E, F, G and H), as shown, to avoid adverse interactions during sterilization.

TABLE 2

| Strain | OD$_{540}$ | Amount of tryptophan, g/l |
|---|---|---|
| SV164(P$_{tac\text{-}ideal}$ΔaroG4-serA5) | 16.9 ± 0.5 | 3.8 ± 0.1 |
| SV164(P$_{tac\text{-}ideal}$→aroG4-serA5)-ΔydiB | 17.2 ± 0.3 | 4.1 ± 0.1 |

Example 7

Construction of a Strain with Inactivated ydiN and ydiB Genes

1. Deletion of the ydiN and the ydiB Genes

The ydiN and the ydiB genes were deleted by the "Red-driven integration". The DNA fragment containing the Cm$^R$ marker encoded by the cat gene was obtained by PCR, using primers P5 (SEQ ID NO: 9) and P10 (SEQ ID NO: 14), and the pMW118-attL-Cm-attR plasmid as a template. Conditions for PCR were as follows: denaturation step for 3 min at 95° C.; profile for two first cycles: 1 min at 95° C., 30 sec at 50° C., 40 sec at 72° C.; profile for the last 25 cycles: 30 sec at 95° C., 30 sec at 54° C., 40 sec at 72° C.; final step: 5 min at 72° C.

An 1711-bp PCR product (FIG. 1) was obtained and purified in agarose gel and was used for electroporation of the *E. coli* strain MG1655, which contains the pKD46 plasmid having a temperature-sensitive replication origin. The pKD46 plasmid is necessary for integration of the PCR product into the chromosome of the MG1655 strain.

Electrocompetent cells were prepared as follows: *E. coli* MG1655/pKD46 was grown overnight at 30° C. in LB medium containing ampicillin (100 mg/l), and the culture was diluted times with 5 ml of SOB medium containing ampicillin and L-arabinose (1 mM). The cells were grown with aeration at 30° C. to an OD$_{600}$ of ≈0.6 and then were made electrocompetent by concentrating 100-fold and washing three times with ice-cold deionized H$_2$O. Electroporation was performed using 70 μl of cells and 100 ng of the PCR product. Cells after electroporation were incubated with 1 ml of SOC medium at 37° C. for 2.5 hours and then were plated onto L-agar containing chloramphenicol (30 μg/ml) and grown at 37° C. to select Cm$^R$ recombinants. Then, to eliminate the pKD46 plasmid, two passages on L-agar with Cm at 42° C. were performed and the obtained colonies were tested for sensitivity to ampicillin.

2. Verification of the ydiN and the ydiB Genes Deletion by PCR

The mutants having the ydiN and the ydiB genes deleted and marked with the Cm resistance gene were verified by PCR. Locus-specific primers P7 (SEQ ID NO: 11) and P12 (SEQ ID NO: 16) were used in PCR for verification. Conditions for PCR verification were as follows: denaturation step for 3 min at 94° C.; profile for 30 cycles: 30 sec at 94° C., 30 sec at 54° C., 1 min at 72° C.; final step: 7 min at 72° C. The PCR product using the parental ydiB$^+$ strain MG1655 as a template, was 2339 bp in length. The PCR product obtained using the mutant strain as the template was 1900 bp in length (FIG. 2). The mutant strain was named MG1655 ΔydiNB::cat.

Example 8

Production of L-phenylalanine by *E. coli* Strain AJ12739-ΔydiNB

To test the effect of inactivation of the ydiN and the ydiB genes on L-phenylalanine production, DNA fragments from the chromosome of the above-described *E. coli* MG1655 ΔydiNB::cat can be transferred to the phenylalanine-producing *E. coli* strain AJ12739 by P1 transduction to obtain strain AJ12739-ΔydiNB::cat.

Furthermore, Cm resistance gene (cat gene) can be eliminated from the chromosome of the strain AJ12739-ΔydiNB::cat using the int-xis system. For that purpose the strain AJ12739-ΔydiNB::cat can be transformed with the pMWts-Int/Xis plasmid. Transformant clones can be selected on the LB-medium containing 100 μg/ml of ampicillin. Plates can be incubated overnight at 30° C. Transformant clones can be cured from the cat gene by spreading the separate colonies at 37° C. (at that temperature repressor CIts is partially inactivated and transcription of the int/xis genes is derepressed) followed by selection of the Cm$^S$Ap$^R$ variants. Elimination of the cat gene from the chromosome of the strain can be verified by PCR. Locus-specific primers P7 (SEQ ID NO: 11) and P12 (SEQ ID NO: 16) can be used in PCR for verification. Conditions for PCR verification can be as described above. The PCR product obtained in reaction with cells not having the cat gene should be 294 bp in length. Thus, the strain AJ12739-ΔydiNB with the inactivated ydiN and ydiB genes and the eliminated cat gene can be obtained.

Both strains, AJ12739-ΔydiNB and AJ12739, can each be cultivated at 37° C. for 18 hours in a nutrient broth, and 0.3 ml of the obtained culture can each be inoculated into 3 ml of a fermentation medium in a 20×200-mm test tube and cultivated at 37° C. for 48 hours with shaking on a rotary shaker. After cultivation, the amount of phenylalanine which accumulates in the medium can be determined by TLC as described in Example 2.

The composition of the fermentation medium (g/l) is as follows:

| | |
|---|---|
| Glucose | 40.0 |
| $(NH_4)_2SO_4$ | 16.0 |
| $K_2HPO_4$ | 0.1 |
| $MgSO_4 \cdot 7H_2O$ | 1.0 |
| $FeSO_4 \cdot 7H_2O$ | 0.01 |
| $MnSO_4 \cdot 5H_2O$ | 0.01 |
| Thiamine HCl | 0.0002 |
| Yeast extract | 2.0 |
| Tyrosine | 0.125 |
| $CaCO_3$ | 20.0 |

Glucose and magnesium sulfate are sterilized separately. $CaCO_3$ is dry-heat sterilized at 180° C. for 2 hours. The pH is adjusted to 7.0.

Example 9

Production of L-tryptophan by *E. coli* strain SV164 ($P_{tac\text{-}ideal}$→-aroG4-serA5)-ΔydiNB To test the effect of inactivation of the ydiN and the ydiB genes on L-tryptophan production, DNA fragments from the chromosome of the above-described *E. coli* strain MG1655 ΔydiNB::cat can be transferred to the tryptophan-producing *E. coli* strain SV164 ($P_{tac\text{-}ideal}$→aroG4-serA5) by P1 transduction to obtain the strain SV164($P_{tac\text{-}ideal}$→aroG4-serA5)-ΔydiNB::cat.

Furthermore, the Cm resistance gene (cat gene) can be eliminated from the chromosome of the SV164($P_{tac\text{-}ideal}$→aroG4-serA5)-ΔydiNB::cat strain using the int-xis system. For that purpose, the SV164($P_{tac\text{-}ideal}$→aroG4-serA5)-ΔydiNB::cat strain can be transformed with the pMWts-Int/Xis plasmid. Transformant clones can be selected on the LB-medium containing 100 μg/ml of ampicillin. Plates can be incubated overnight at 30° C. Transformant clones can be cured from the cat gene by spreading the separate colonies at 37° C. (at that temperature, the repressor CIts is partially inactivated and transcription of the int/xis genes is derepressed) followed by selection of $Cm^S Ap^R$ variants. Elimination of the cat gene from the chromosome of the strain can be verified by PCR. Locus-specific primers P7 (SEQ ID NO: 11) and P12 (SEQ ID NO: 16) can be used in PCR for verification. Conditions for PCR verification can be as described above. The PCR product using the cells not having the cat gene, should be 294 bp in length. Thus, the SV164($P_{tac\text{-}ideal}$→aroG4-serA5)-ΔydiNB strain with the inactivated ydiN and the ydiB genes and the eliminated cat gene can be obtained.

Both of the SV164($P_{tac\text{-}ideal}$→aroG4-serA5)-ΔydiNB and SV164($P_{tac\text{-}ideal}$→-aroG4-serA5) strains can each be cultivated with shaking at 32° C. for 18 hours in 3 ml of nutrient broth. The obtained cultures (0.3 ml each) can be inoculated into 3 ml of a fermentation medium in 20×200-mm test tubes, and cultivated at 32° C. for 72 hours with a rotary shaker at 250 rpm. After cultivation, the amount of tryptophan which accumulates in the medium can be determined by TLC as described in Example 2.

The fermentation medium components are listed in Table 1, but should be sterilized in separate groups (A, B, C, D, E, F, G and H), as shown, to avoid adverse interactions during sterilization.

While the invention has been described in detail with reference to preferred embodiments thereof, it will be apparent to one skilled in the art that various changes can be made, and equivalents employed, without departing from the scope of the invention. All the cited references herein are incorporated as a part of this application by reference.

INDUSTRIAL APPLICABILITY

According to the present invention, production of an aromatic L-amino acid by a bacterium of the Enterobacteriaceae family can be enhanced.

The invention claimed is:

1. An aromatic L-amino acid-producing *Escherichia coli* bacterium, wherein said bacterium has been modified to attenuate expression of a gene selected from the group consisting of *Escherichia coli* ydiN, *Escherichia coli* ydiB, and combinations thereof.

2. The bacterium according to claim 1, wherein said expression is attenuated by inactivating said gene.

3. The bacterium according to claim 1, wherein said aromatic L-amino acid is selected from the group consisting of L-phenylalanine, L-tyrosine, and L-tryptophan.

4. A method for producing an aromatic L-amino acid comprising:
cultivating the bacterium according to claim 1 in a medium, and
collecting said aromatic L-amino acid from the medium.

5. The method according to claim 4, wherein said aromatic L-amino acid is selected from the group consisting of L-phenylalanine, L-tyrosine, and L-tryptophan.

6. A method for producing a lower alkyl ester of α-L-aspartyl-L-phenylalanine comprising:
A) cultivating the bacterium according to claim 1 in a culture medium to produce and accumulate L-phenylalanine in the medium, and
B) synthesizing the lower alkyl ester of α-L-aspartyl-L-phenylalanine from aspartic acid or its derivative and the accumulated L-phenylalanine,
wherein said bacterium is able to produce L-phenylalanine.

7. The method according to claim 6, further comprising:
A) esterifying the accumulated L-phenylalanine to generate a lower alkyl ester of L-phenylalanine,
B) condensing the lower alkyl ester of L-phenylalanine with N-acyl-L-aspartic anhydride to generate a lower alkyl ester of N-acyl-α-L-aspartyl-L-phenylalanine,
C) separating the lower alkyl ester of N-acyl-α-L-aspartyl-L-phenylalanine from the culture medium, and
D) hydrogenating the lower alkyl ester of N-acyl-α-L-aspartyl-L-phenylalanine to generate the lower alkyl ester of α-L-aspartyl-L-phenylalanine.

8. A method for producing an aromatic L-amino acid comprising:
cultivating the bacterium according to claim 2 in a medium, and
collecting said aromatic L-amino acid from the medium.

9. The method according to claim 8, wherein said aromatic L-amino acid is selected from the group consisting of L-phenylalanine, L-tyrosine, and L-tryptophan.

10. A method for producing a lower alkyl ester of α-L-aspartyl-L-phenylalanine comprising:
A) cultivating the bacterium according to claim 2 in a culture medium to produce and accumulate L-phenylalanine in the medium, and
B) synthesizing a lower alkyl ester of α-L-aspartyl-L-phenylalanine from aspartic acid or its derivative and the accumulated L-phenylalanine,
wherein said bacterium is able to produce L-phenylalanine.

11. The method according to claim 10, further comprising:
A) esterifying the accumulated L-phenylalanine to generate a lower alkyl ester of L-phenylalanine,
B) condensing the lower alkyl ester of L-phenylalanine with N-acyl-L-aspartic anhydride to generate a lower alkyl ester of N-acyl-α-L-aspartyl-L-phenylalanine,
C) separating the lower alkyl ester of N-acyl-α-L-aspartyl-L-phenylalanine from the culture medium, and
D) hydrogenating the lower alkyl ester of N-acyl-α-L-aspartyl-L-phenylalanine to generate the lower alkyl ester of α-L-aspartyl-L-phenylalanine.

* * * * *